US006475492B1

(12) United States Patent
Philipp et al.

(10) Patent No.: US 6,475,492 B1
(45) Date of Patent: Nov. 5, 2002

(54) PEPTIDES AND ASSAYS FOR THE DIAGNOSIS OF LYME DISEASE

(75) Inventors: Mario T. Philipp, Mandeville, LA (US); Fang Ting Liang, Covington, LA (US)

(73) Assignee: The Administrators of the Tulane Educational Fund, New Orleans, LA (US)

(*) Notice: Subject to any disclaimer, the term of this patent is extended or adjusted under 35 U.S.C. 154(b) by 0 days.

(21) Appl. No.: 09/300,971

(22) Filed: Apr. 28, 1999

(51) Int. Cl.[7] .................. A61K 39/02; A61K 38/00; C07K 5/00

(52) U.S. Cl. .................. 424/234.1; 514/2; 530/300; 530/806

(58) Field of Search .................. 514/2; 530/300, 530/806; 424/234.1

(56) References Cited

U.S. PATENT DOCUMENTS 6,083,722 A  *  7/2000  Bergstrom et al. ......... 435/69.3

FOREIGN PATENT DOCUMENTS

| CH | 485551 | 2/1990 |
|---|---|---|
| EP | 339695 | 11/1989 |
| EP | 465204 | 1/1992 |
| WO | WO 90/04411 | 5/1990 |
| WO | WO 91/09870 | 7/1991 |
| WO | WO 91/13630 | 9/1991 |
| WO | WO 92/00055 | 1/1992 |
| WO | WO 97/31123 | * 8/1997 |
| WO | WO 99/00413 | 1/1999 |

OTHER PUBLICATIONS

Abbas et al, Cellular and Molceular Immunology, (textbook), p. 315, 1991.*
Bowie et al, "Deciphering the Message in Protein Sequences: Tolerance to Amino Acid Substitutions", Science, vol. 247, pp. 1306–1310, 1990.*
Burgess et al, "Possible Dissociation of the Heparin–binding and Mitogenic Activities of Heparin–binding Growth Factor–1 . . ." Journ Cell Biol, vol. 111, pp. 2129–2138, Nov. 1990.*
Lazar et al, "Transforming Growth Factor Alpha: Mutation of Aspartic Acid 47 and Leucine 48 Result in Different Biological Activities", Mol Cell Biol, vol. 8, No. 3, pp. 1247–1252, Mar. 1988.*
M. Philipp et al., "Safety and Immunogenicity of Recombinant Outer Surface Protein A (OspA) Vaccine Formulations in the Rhesus Monkey," *J. Spirochetal and Tick–borne Disease, 3:*67–79 (Mar. 1996).
A. DeSilva et al., "*Borrelia burgdorferi* OspA is an Arthropod–specific Transmission–blocking Lyme Disease Vaccine," *J. Exp. Med., 183:*271–275 (Jan. 1996).

T. Mather et al., "Ixodes Saliva: Vector Competence for *Borrelia burgdorferi* and Potential Vaccine Strategies", in VII International Congress on Lyme Borreliosis, San Francisco, CA 1996.
A. Sădžiene et al., "Antibody–resistant Mutants of *Borrelia burgdorferi:* In Vitro Selection and Characterization," *J. Exp. Med., 176:*799–809 (Sep. 1992).
A. DeSilva et al., "Growth and Migration of *Borrelia burgdorferi* in Ixodes Ticks During Blood Feeding," *Am. J. Trop. Med., 53:*397–404 (Oct. 1995).
P. Rosa et al., "Recombination between Genes Encoding Major Outer Surface Proteins A and B of *Borrelia burgdorferi,*" *Mol. Microbial. 6:*3031–3040 (1992).
T. Schwan et al., "Distribution and Molecular Analysis of Lyme Disease Spirochetes, *Borrelia burgdorferi,* Isolated from Ticks throughout California," *J. Clin. Microbiol., 31:*3096–3108 (Dec. 1993).
H. Kawabata et al., "Genetic and Immunological Analyses of VIs (VMP–like sequences) of *Borrelia burgdorferi,*" *Microb. Pathog., 24:*155–166 (Mar. 1998).
A.G. Barbour et al., "Variation in a Major Surface Protein of Lyme Disease Spirochete," *Infect. Immun., 45:*94–100 (Jul. 1984).
W.J. Simpson et al., "Reactivity of Human Lyme Borreliosis Sera with a 39–Kilodalton Antigen Specific to *Borrelia burgdorferi,*" *J. Clin. Microbiol., 28:*1329–1337 (Jun. 1990).
K. Hansen et al., "Immunochemical Characterization of and Isolation of the Gene for a *Borrelia burgdorferi* Immunodominant 60–Kilodalton Antigen Common to a Wider Range of Bacteria," *Infect. Immun., 56:*2047–2053 (Aug. 1988).
K. Hansen et al., "Measurement of Antibodies to the *Borrelia burgdorferi* Flagellum Improves Serodiagnosis in Lyme Disease," *J. Clin. Microbiol., 26:*338–346 (Feb. 1988).
B. Wilske et al., "Immunochemical and Immunological Analysis of European *Borrelia burgdorferi* Strains," *Zbl. Bakt. Hyg. A., 263:*92–102 (1986).
D. W. Dorward et al., "Immune Capture and Detection of *Borrelia burgdorferi* Antigens in Urine, Blood, or Tissues from Infected Ticks, Mice, Dogs, and Humans," *J. Clin. Microbiol., 29:*1162–1170 (Jun. 1991).

(List continued on next page.)

*Primary Examiner*—Anthony C Caputa
*Assistant Examiner*—Karen A. Canella
(74) *Attorney, Agent, or Firm*—Howson and Howson

(57) ABSTRACT

A peptide consisting of an invariable 26-amino-acid-long region, named $IR_6$, which is antigenically conversed among strains and species of the *B. burgdorferi sensu lato* complex, and immunodominant in both human and nonhuman primate hosts is described. This peptide is characterized by the sequence MKKDDQIAAAMVLRGMAKDGQFALKD (SEQ ID NO:1). This peptide is useful for rapid and specific diagnosis of Lyme disease, as are proteins containing this peptide and nucleic acid sequences encoding this peptide and these proteins.

28 Claims, 7 Drawing Sheets

OTHER PUBLICATIONS

L. Bakken et al., "Interlaboratory Comparison of Test Results for Detection of Lyme Disease by 516 Participants in the Wisconsin State Laboratory of Hygiene/College of American Pathologist Proficiency Testing Program," *J. Clin. Microbiol., 35:*537 (Mar. 1997).

M. Kay et al., "In vivo Hepatic Gene Therapy: Complete Albeit Transient Correction of Factor IX Deficiency in Hemophilia B Dogs," *Proc. Natl. Acad. Sci. USA, 91:*2353 (Mar. 1994).

S. Ishibashi et al., "Hypercholesterolemia in Low Density Lipoprotein Receptor Knockout Mice and its Reversal by Adenovirus–Mediated Gene Delivery," *J. Clin. Invest., 92:*883 (Aug. 1993).

J.R. Zhang et al., "Antigenic Variation in Lyme Disease Borreliae by Promiscuous Recombination of VMP–like Sequence Cassettes," *Cell, 89:*275–285 (Apr. 18, 1997).

J.R. Zhang et al., "Kinetics and In Vivo Induction of Genetic Variation of vlse in *Borrelia burgdorferi,*" *Infect. Immun., 66*(8):3689–3697 (Aug. 1998).

J. R. Zhang et al., "Genetic Variation of the *Borrelia burgdorferi* Gene vlsE Involves Cassette–Specific, Segmental Gene Conversion," *Infect. Immun., 66:*3698–3704 (Aug. 1998).

J.R. Zhang et al., "Kinetics and in vivo Induction of vlsE Antigenic Variation in *Borrelia burgdorferi*" EMBL/GenBank/DDBJ databases, Accession No. AF034515 (Jun. 2, 1998).

J.R. Zhang et al., "Kinetics and in vivo Induction of vlsE Antigenic Variation in *Borrelia burgdorferi*", EMBL/GenBank/DDBJ databases, Accession No. AF034523 (Jun. 2, 1998).

J.R. Zhang et al., "Kinetics and in vivo Induction of vlsE Antigenic Variation in *Borrelia burgdorferi*", EMBL/GenBank/DDBJ databases, Accession No. AF034525 (Jun. 2, 1998).

D. L. Cox et al., "Limited Surface Exposure of *Borrelia burgdorferi* Outer Surface Lipoproteins," *Proc. Natl. Acad. Sci. USA, 93:*7973–7978 (Jul. 1996).

S. M. Kochi et al., "Facilitation of Complement–Dependent Killing of the Lyme Disease Spirochete, *Borrelia burgdorferi*, by Specific Immunoglobulin G Fab Antibody Fragments," *Infect. Immun., 61:*2532–2536 (Jun. 1993).

D.M. Reinitz et al., "Variable and Conserved Structural Elements of Trypanosome Variant Surface Glycoproteins," *Mol. Biochem. Parasitol., 51:*119–132 (Feb. 1992).

K.T. Forest et al., "Assembly and Antigenicity of the *Neisseria gonorrhoeae* Pilus Mapped with Antibodies," *Infect. Immun., 64:*644–652 (Feb. 1996).

P. Marrack and J. Kappler, "Subversion of the Immune System by Pathogens," *Cell, 76:*323–332 (Jan. 28, 1994).

R. R. Garrity et al., "Refocusing Neutralizing Antibody Response by Targeted Dampening of an Immundominant Epitope," *J. Immunol., 159:*279–289 (Jul. 1, 1997).

J.G. Donahue et al., "Reservoir Competence of White–Footed Mice for Lyme Disease Spirochetes," *Am. J. Trop Med. Hyg.,*36:92–96 (Jan. 1987).

R. T. Green et al., "Immunoblot Analysis of Immunoglobulin G Response to the Lyme Disease Agent (*Borrelia burgdorferi*) in Experimentally and Naturally Exposed Dogs," *J. Clin. Micro., 26:*648–653 (Apr. 1988).

Lightfoot et al., "Empiric Parenteral Antibiotic Treatment of Patients with Fibromyalgia and Fatigue and a Positive Serlogic Result for Lyme Disease," *Ann. Intern Med., 129:*503–509 (Sep. 15, 1993).

Tugwell et al., "Laboratory Evaluation in the Diagnosis of Lyme Disease," *Ann. Intern. Med., 127:*1109–1123 (Dec. 15, 1997).

Ramamoorthy et al., "Molecular Characterization, Genomic Arrangement, and Expression of bmpD, a New Member of the bmp Class of Genes Encoding Membrane Proteins of *Borrelia burgdorferi,*" *Infect. Immun., 64*(4):1259–1264 (Apr. 1996).

H. Kawabata et al., "Genetic and Immunological Analyses of Vls (VMP–like Sequences) of *Borrelia burgdorferi*", EMBL/GenBank/DDBJ databases. Accession No. AB011063 (Mar. 13, 1998).

E. Fikrig et al., "*Borrelia burgdorferi* P35 and P37 Proteins Expressed in Vivo, Elicit Protective Immunity", *Immunity, 6:*531–539 (May 1997).

A. Aberer et al., "Molecular Mimicry and Lyme Borreliosis: A Shared Antigenic Determinant Between *Borrelia burgdorferi* and Human Tissue",*Ann. Neurol., 26:*732–737 (Dec. 1989).

G. S. Gassmann et al., "N–Terminal Amino Acid Sequences of the *Borrelia burgdorferi* Flagellin", *FEMS Microbiol. Lett., 60:*101–106 (Jul. 1, 1989).

\* cited by examiner

FIGURE 2

```
               10         20         30         40         50         60
P7-1    KNNDHKNHKG TVKNAVDMAK AAEEAASAAS AATGNAAIGD VVKNSGAAAK GGEAASVNGI
B31 Vls            A*SGEQILSA IVKA**AG*A DQD*EKPG-* AKNPIA**IG K*N*DDGADF 70         80         90        100        110        120
P7-1    AKGIKGIVDA AGKADAKEGK LDATGAEGTT NVNAGKLFVK RAADDGGDAD DAGKAAAAVA
297 Vls                                                      ATE**TA*
B31 Vls GD*M*K-D*Q IAA*I*LR*M -AKD*KFAVK KDEK**A--E G*IKGASELL *KLVK*VKT*

130  IR₁  140        150  IR₂  160        170        180
P7-1    ASAATGNAAI GDVVNGDVAK AKGGDAASVN GIAKGIKGIV DAAEKADAKE GKLNAAGAEG
297 Vls SGDKEMIGKV VK*TNAGA*A **EEK* *S** E*G- *EAGD*
B31 Vls EG*SS*T*** *E**DN-A-A -*AA*KD**T *******E** E**G--GSE- K-*KV*A*K*
                            VR₁                                  VR_II

190  IR₃  200        210  IR₄  220        230        240
P7-1    TTNADAGKLF VKNAGNVGGE AGDAGKAAAA VAAVSGEQIL KAIVHAAKDG GEKQGKKAAD
297 Vls NKD*C***** A***A*G**G *AA*E***** *S****K*** ****D**G-K E**GVADVKE
B31 Vls EN*KG***** G*AGA*AH*D SEA*S***G* *S******** S***K**GEA *DQE***PEE
                            VR_III                                VR_IV

IR₅   250        260        270  IR₆  280        290        300
P7-1    ATNPIDAAIG GAGDNDAAAA FATMKKDPQI AAAMVLRGMA KDGQFALKDA AAAHEGTVKN
297 Vls ***E ST***F QDE*N* *I**** *E*****N EHDKAKGL*S
B31 Vls *K*A DKD-GEFN QDG***** *IA*** *KVG GEKA**AI*G
                            VR_V                                  VR_VI 310        320        330        340
P7-1    AVDIIKAAAE AASAASAATG SAAIGDVVNG NGATAKGGDA KSVNGIAKG
297 Vls T*E
B31 Vls VSELLDLVKA VKT*EK*SS* T**EA- DA-A-*VA*K AT***
```

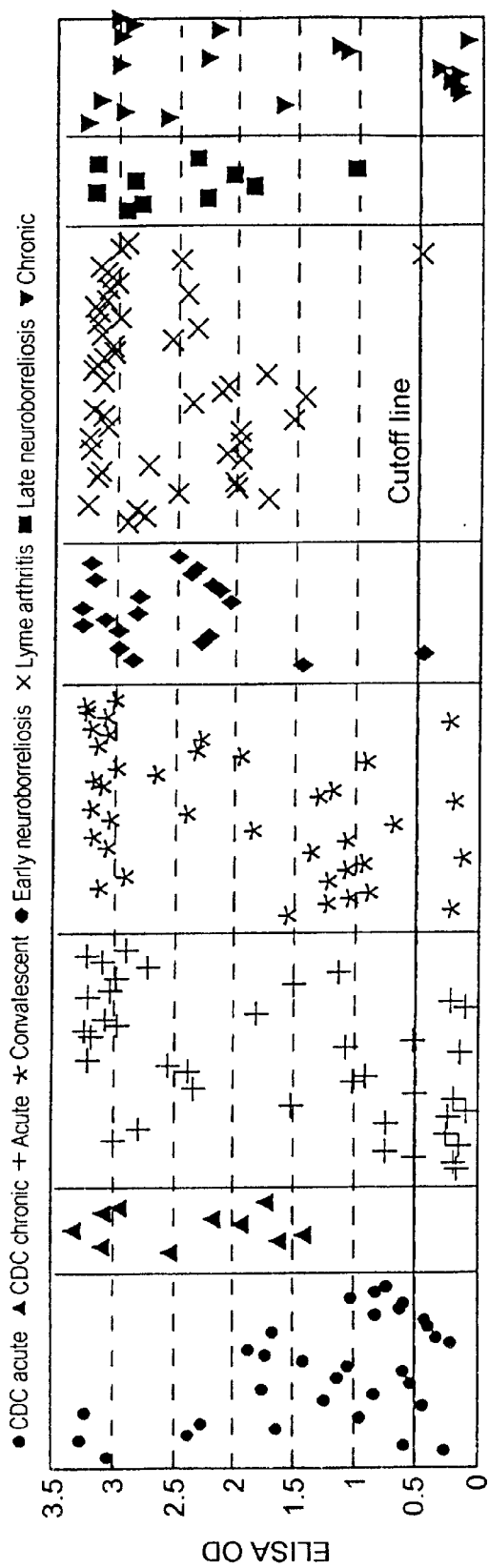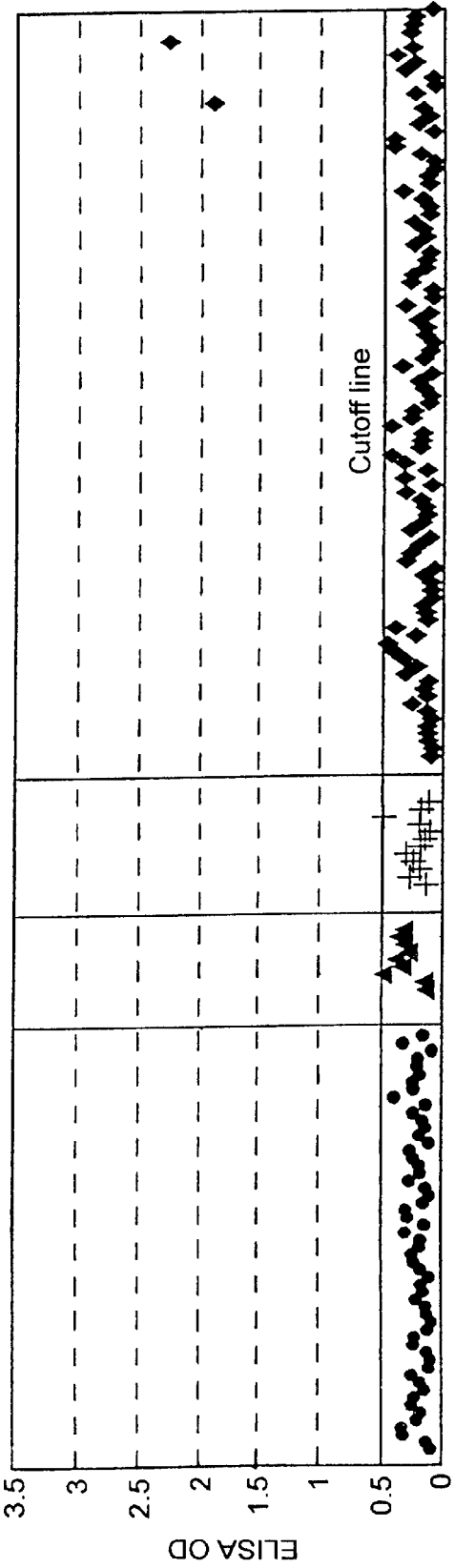
FIG. 8A
FIG. 8B

PEPTIDES AND ASSAYS FOR THE DIAGNOSIS OF LYME DISEASE

This invention was funded in part by the National Institutes of Health Grant Nos. ROI AI35027 and RR00164. The United States government has certain rights in this invention.

FIELD OF THE INVENTION

The present invention relates generally to the field of diagnostic compositions and methods useful in the diagnosis of Lyme borreliosis.

BACKGROUND OF THE INVENTION

The bacterium *Borrelia burgdorferi* (*sensu lato*) is the causative agent of Lyme borreliosis, i.e., Lyme disease. This disease is transmitted by the bite of various species of Ixodes ticks carrying the spirochete. The main reservoir of the infection in the United States is the white footed mouse, *Peromyscus leucopus,* and the infection can be transmitted to many mammalian species including dogs, cats, and man [J. G. Donahue, et al., *Am. J. Trop. Med. Hyg.,* 36:92–96 (1987); R. T. Green, et al, *J. Clin. Micro.,* 26:648–653 (1988)]. Despite the presence of an active immune response, the disease persists for years in patients. Such persistence is postulated to be the result, at least in part, of antigenic variation in the bacterial proteins [J. R. Zhang et al, *Cell,* 89:275–285 (1997)].

Publications relating to proteins and polypeptides of *Borrelia burgdorferi* having suggested their use as diagnostic or pharmaceutical agents. Such proteins and polypeptides include outer surface proteins A and B (OspA and OspB), flagellin, and other proteins designated P21, P39, P66, and P83 according to their estimated molecular weights [A. G. Barbour et al, *Infect. Immun.,* 45:94–100 (1984); W. J. Simpson et al.,*J. Clin. Microbiol.,* 28:1329–1337 (1990); K. Hansen et al., *Infect. Immun.,* 56:2047–2053 (1988); K. Hansen et al.,*Infect. J. Clin. Microbiol.,* 26:338–346 (1988); B. Wilske et al., *Zentral, Bakteriol, Parsitenkd, Infektionshkr, Hyg. Abt.* 1 *Orig. Reihe, A.,* 263:92–102 (1986); D. W. Dorward et al., *J. Clin. Microbiol.,* 29:1162–1170 (1991); published NTIS U.S. patent application No. 485,551; European patent application No. 465,204, published Jan. 8, 1992; International Patent Application No. PCT/US91/01500, published Sep. 19, 1991; International Patent Application No. PCT/EP90/02282, published Jul. 11, 1991; International Patent Application No. PCT/DK89/00248, published May 3, 1990; International patent application No. WO92/00055, published Jan. 9, 1992.]

However, the diagnosis of Lyme disease in humans and animals has been compromised by the lack of definitive serology leading to rapid and accurate testing. Current diagnostic tests suffer from low sensitivity and specificity, as illustrated by a recent survey of diagnostic laboratories' performance issued by the Wisconsin State Laboratory of Hygiene [L. Bakken et al., *J. Clin. Microbiol.,* 35:537 (1997)].

There is thus a need in the art for a simple, sensitive and specific diagnostic composition and method for early detection of Lyme disease.

SUMMARY OF THE INVENTION

The present invention satisfies the need in the art by providing methods and compositions which permit rapid and accurate detection of Lyme disease. The methods and compositions of the invention advantageously avoid serologic cross-reactivity with other conditions, including syphilis, chronic arthritis, and multiple sclerosis, from which differential diagnosis was required using prior art methods.

In one aspect, the invention provides a peptide having the amino acid sequence MKKDDQIAAAMVLRG-MAKDGQALKD [SEQ ID NO:1], termed herein $IR_6$, which is an invariable region which is immunodominant in human and animal Lyme disease patients.

In another aspect, the invention provides an artificial protein which contains the amino acid sequence of $IR_6$, or an analog, homolog or fragment thereof. In one embodiment, this protein may be a fusion protein containing $IR_6$ or a fragment thereof and a fusion partner. In one particularly desirable embodiment, the fusion protein contains a fragment of $IR_6$ corresponding to a T cell epitope, wherein the T cell epitope is fused to a one of the other five invariable regions identified herein ($IR_1$-$IR_5$).

In another desirable embodiment, the artificial protein contains the amino acid sequence of $IR_6$ with an N-terminal amino acid suitable for biotinylation.

In yet another aspect, the invention provides a nucleic acid sequence encoding $IR_6$ peptide or a protein of the invention. In still another aspect, the invention provides a vector comprising a nucleic acid sequence according to the invention under the control of suitable regulatory sequences. In a further aspect, the invention provides a host cell transformed with the vector of the invention.

In a still further aspect, the present invention provides a diagnostic reagent comprising a nucleic acid sequence of the invention and a detectable label which is associated with said sequence.

In yet a further aspect, the invention provides an isolated antibody which is specific for the $IR_6$ peptide of the invention or a fragment thereof. In still a further aspect, the invention provides a diagnostic reagent comprising the antibody of the invention.

In yet another aspect, the invention provides an anti-idiotype antibody specific for the anti-$IR_6$ antibody of the invention and a diagnostic reagent containing the anti-idiotype antibody with a detectable label linked thereto.

In yet a further aspect, the invention provides a method for diagnosing Lyme disease in a human or animal. This method includes the steps of incubating an antigen or antibody of this invention, preferably conventionally labeled for detection, with a sample of biological fluids from a human or an animal to be diagnosed. In the presence of *B. burgdorferi* infection of the human or animal patient, an antigen-antibody complex is formed. Subsequently the reaction mixture is analyzed to determine the presence or absence of these antigen-antibody complexes. In a further embodiment, the diagnostic assay employs DNA sequences, preferably anti-sense sequences, of the antigen or fragments thereof, and diagnoses infection by the presence of sequences in a biological fluid from the patient that hybridizes thereto. Other conventional assay formats may be employed using reagents identified by this invention.

In another aspect the invention provides a kit for diagnosing infection with *B. burgdorferi* in a human or an animal patient sample which contains at least one antibody capable of binding at least one antigen of this invention of antigenic fragment(s) thereof, or a DNA sequence encoding one or more antigen(s) of this invention or an anti-sense sequence thereof. The antibodies and sequences may be optionally labeled for detection, or a detection system may be included in the kit.

In another aspect, the invention provides a therapeutic composition and methods for treating humans and/or animals with Lyme disease. The therapeutic composition contains an antibody, or protein, or fragment as described above and a suitable pharmaceutical carrier.

In a further aspect, the invention provides vaccine compositions and methods of vaccinating a human or animal patient against Lyme Disease by use of these above-described compositions. The vaccine composition may contain the $IR_6$ protein, fragments thereof, fusion proteins or mixtures of proteins as described above with a pharmaceutically acceptable carrier. More preferably, the vaccine compositions contain fusion proteins composed of $IR_6$, or a fragment thereof corresponding to a T cell epitope, fused to a partner such as $IR_1$–$IR_5$.

In yet a further aspect, the invention provides vaccine compositions and methods of vaccinating a human or animal patient against Lyme Disease by use of nucleic acid compositions, e.g. DNA vaccines. The compositions contain an effective amount of a DNA sequence encoding at least one $IR_{1-5}$ or $IR_6$ peptide or protein of this invention and a pharmaceutically acceptable carrier.

Other aspects and advantages of the present invention are described further in the following detailed description of the preferred embodiments thereof.

BRIEF DESCRIPTION OF THE DRAWINGS

FIG. 2 provides a comparison among deduced amino acid sequences of P7-1 (SEQ ID NO:9) and cassette segments from VlsE of strains B31 (SEQ ID NO:11) and 297 (SEQ ID NO:10) of *B. burgdorferi*. The B31 cassette segment is confined between the repeat sequence EGAIKG, single underlined. Variable regions ($VR_{1-VI}$) are doubly underlined and invariable regions ($IR_{1-6}$) are shaded. Sequence alignment was obtained with the pam250 algorithm. Identical amino acids are indicated with asterisks and sequence gaps with dashes; non-identical residues are shown as letters following the single letter code.

FIGS. 8A–8B illustrate the sensitivity of the $IR_6$ peptide ELISA of the invention. See, Example 8.

DETAILED DESCRIPTION OF THE INVENTION

Figure 1:
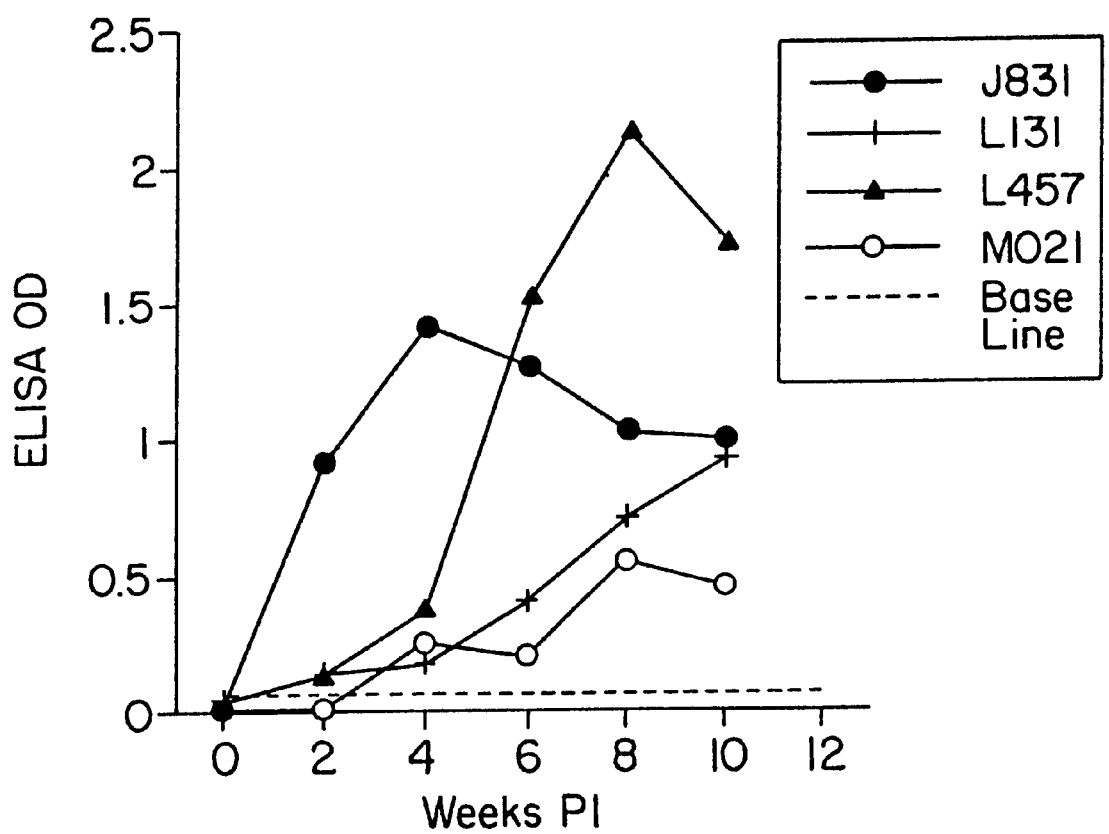
FIG. 1 illustrates an antibody response to P7-1 in monkeys. Serum samples from two rhesus macaques that were infected with HK1 strain of *B. burgdorferi* (J831 and L131) and two that were infected with B31 strain spirochetes (L457 and M021) were serially collected. The Ab level was measured by ELISA using P7-1 as Ag. The baseline represents the mean ELISA OD of serum samples collected from all of the animals before infection plus 3 SDs.

The present invention satisfies the need in the art by providing methods and compositions which permit rapid and accurate detection of Lyme disease. The methods and compositions of the invention advantageously avoid serologic cross-reactivity with other conditions, including syphilis, chronic arthritis, and multiple sclerosis, from which differential diagnosis was required using prior art methods.

In a currently preferred embodiment, the invention provides a peptide-based ELISA, which in terms of simplicity, specificity and sensitivity, is superior to current serologic diagnostic methods for Lyme disease. Further; the ELISA of the invention is also useful in serum samples that contain anti-OspA antibodies, permitting diagnosis of Lyme disease in individuals who have been exposed (either naturally or through vaccination) with *B. burgdorferi*, the causative agent of Lyme disease.

The methods and compositions of the invention utilize a peptide having the amino acid sequence MKKDD-QIAAAMVLRGMAKDGQFALKD (SEQ ID NO:1], which provides the specificity for Lyme disease which is an advantage of the invention. Also provided by the present invention are proteins containing this peptide, as well as antibodies directed thereto and nucleic acid sequences encoding these peptides and/or proteins for use in diagnostic, therapeutic and prophylactic compositions and methods for the treatment or prevention of Lyme Disease the invention provide advantages over the use of other Borrelia proteins and antibodies in known compositions and methods for this purpose.

I. The Invariable Region Peptides, Proteins, and Nucleic Acids of the Invention

The present invention relates to six antigenic peptides which correspond to invariable regions ($IR_{1-6}$), found within the variable domain of the variable surface antigen of *B. burgdorferi* (VlsE). These IRs are conserved among strains and genospecies of the *B. borgdorferi* sensu lato complex. Surprisingly, unlike the variable regions of several other major proteins, which are not antigenic in natural infections, the most conserved of the IRs, $IR_6$, is immunodominant in Lyme disease patients and in animals infected with *B. burgdorferi*. $IR_6$ is exposed on the surface of VlsE, as assessed by immunoprecipitation experiments, but is inaccessible to antibody on the spirochete's outer membrane, as demonstrated by immunofluorescence and in vitro killing assays.

Thus, the present invention provides six novel peptides and fragments thereof which may be used in a variety of diagnostic assays and compositions. Of these peptides, the $IR_6$ peptide and proteins containing this peptide or fragments thereof are particularly well suited for use in specific diagnosis of Lyme disease. Although less desirable, the peptides $IR_{1-5}$ may also be used for such a purpose. The peptides $IR_{1-5}$ described herein and proteins containing this peptide or fragments thereof are particularly well suited for use in therapeutic and pharmaceutical compositions for the treatment of Lyme disease. Although less desirably, $IR_6$ may also be used for such purposes.

A. Protein and Peptide Sequences

For convenience throughout this specification, reference will be made to "$IR_{1-5}$ or $IR_6$ peptides and proteins", but it will be understood that this term encompasses the fragments, analogs, modified peptides and proteins, fusion proteins, and other amino acid constructs of the invention, except where otherwise specified.

In one aspect, the invention provides novel peptides having the amino sequences provided below, utilizing standard single letter amino acid codes.

$IR_1$: GNAAIGDVV [SEQ ID NO:3]

$IR_2$: SVNGIAKGIKGIVDAA [SEQ ID NO:4]

$IR_3$: AGKLFVK [SEQ ID NO:5]

$IR_4$: DAGKAAAAVAAVSGEQILKAIVHAA [SEQ ID NO:6]

$IR_5$: ATNPIDAAIG [SEQ ID NO:7] and $IR_6$: MKKDDQIAAAMVLRGMAKDGQFALKD [SEQ ID NO:8].

These peptide antigens may be isolated in a form substantially free from other proteinaceous and non-proteinaceous material so the microorganism and the tick vector. The antigens may be isolated from the spirochete and further purified using any of a variety of conventional methods including: liquid chromatography such as normal or reversed phase, using HPLC, FPLC and the like; affinity chromatography (such as with inorganic ligands or monoclonal antibodies); size exclusion chromatography; immobilized metal chelate chromatography; gel electrophoresis; and the like. One of skill in the art may select the most appropriate isolation and purification techniques without departing from the scope of this invention.

Alternatively, the peptides and proteins of the invention, described below, may be produced recombinantly following conventional genetic engineering techniques [see e.g., Sambrook et al, Molecular Cloning: A Laboratory Manual, Cold Spring Harbor Laboratories, Cold Spring Harbor, N.Y. and the detailed description of making the proteins below]. In still another alternative, the peptides and proteins of the invention may be produced using conventional chemical synthesis techniques, such as those described in G. Barony and R. B. Merrifield, The Peptides: Analysis, Synthesis & Biology, Academic Press, pp. 3–285 (1980), among others. The term "artificial" is used herein to denote the preparation of the construct (e.g., a peptide, protein, nucleic acid, or antibody of the invention) by chemical synthesis, recombinant technology, or other similar means.

The present invention further provides analogs, fragments, and mutant peptides, as well as proteins containing $IR_{1-6}$, or such analogs, fragments or mutants, as described below.

i. Analogs and Modified Peptide and Protein Antigens

Analogs or modified versions of the peptides $IR_{1-6}$ are provided. Typically, analogs differ from the specifically identified proteins by only one to four codon changes. Examples include polypeptides with minor amino acid variations from the illustrated partial amino acid sequence of, for example, $IR_2$ having conservative amino acid replacements. Conservative replacements are those that take place within a family of amino acids that are related in their side chains and chemical properties. Also provided are homologs of the proteins of the invention which are characterized by having at least 90% identity, and more preferably 95–99% identity with $IR_1$ the sequences of the vls-like proteins. Based on the sequence information provided herein, one of skill in the art can readily obtain full-length homologs and analogs.

As known in the art, "homology" or "identity" means the degree of sequence relatedness between two peptides or two nucleotide sequences as determined by the identity of the match between two lengths of such sequences. Both identity and homology can be readily calculated by methods extant in the prior art [See, e.g., COMPUTATIONAL MOLECULAR BIOLOGY, Lesk, A. M. ed., Oxford University Press, New York, (1988); BIOCOMPUTING: INFORMATICS AND GENOME PROJECTS, Smith, D. W. ed., Academic Press, New York, (1993); COMPUTER ANALYSIS OF SEQUENCE DATA, PART I, Griffin, A. M., and Griffin, H. G., eds. Humana Press, New Jersey, (1994); SEQUENCE ANALYSIS IN MOLECULAR BIOLOGY, von Heinje, G., Academic Press, (1987); and SEQUENCE ANALYSIS PRIMER, Gribskov, M. and Devereux, J., eds. M Stockton Press, New York (1991)]. While there exist a number of methods to measure identity and homology between two nucleotide sequences, the terms "identity", "similarity" and homology are well known to skilled artisans [H. Carillo and D. Lipton, *SIAM J. Applied Math.*, 48:1073 (1988)]. Methods commonly employed to determine identity or homology between two sequences include, but are not limited to, those disclosed in Guide to Huge Computers, Martin J. Bishop, ed., Academic Press, San Diego, 1994, and H. Carillo and D. Lipton, *SIAM J. Applied Math.*, 48:1073 (1988). Preferred methods to determine identify or homology are designed to give the largest match between the two sequences tested. Methods to determine identity and similarity are codified in computer programs. Preferred computer program methods to determine identity and homology between two sequences include, but are not limited to, the algorithm BESTFIT from the GCG program package [J. Devereux et al., *Nucl. Acids Res.*, 12(1):387 (1984)], the related MACVECTOR program (Oxford), and the FASTA (Pearson) programs, which may be used at default settings or modified setting such as determined to be suitable by one of skill in the art.

An $IR_{1-5}$ or $IR_6$ peptide or protein of the present invention may also be modified to increase its immunogenicity. For example, the antigen may be coupled to a chemical compounds or immunogenic carriers, provided that the coupling does not interfere with the desired biological activity of either the antigen or the carrier. For a review of some general considerations in coupling strategies, see *Antibodies, A Laboratory Manual,* Cold Spring Harbor Laboratory, ed. E. Harlow and D. Lane (1988). Useful immunogenic carriers known in the art, include, without limitation, keyhole limpet hemocyanin (KLH); bovine serum albumin (BSA), ovalbumin, PPD (purified protein derivative of tuberculin); red blood cells; tetanus toxoid; cholera toxoid; agarose beads; activated carbon; or bentonite. Useful chemical compounds for coupling include, without limitation, dinitrophenol groups and arsonilic acid.

The $IR_{1-6}$ peptides and proteins of the invention may also be modified by other techniques, such as by denaturation with heat and/or SDS. Alternatively, the peptides and proteins of the invention may be modified to provide an additional N- or C-terminal amino acid sequence suitable for biotinylation, e.g., cysteine or lysine.

ii. Fragments/Deletion Mutants

Further encompassed by this invention are additional fragments of the $IR_{1-5}$ peptides, the $IR_6$ peptide or of the other proteins identified herein. Such fragments are desirably characterized by having a biological activity similar to that displayed by the complete protein, including, e.g., the ability to induce antibodies to the causative agent of Lyme Disease. These fragments may be designed or obtained in any desired length, including as small as about 5–8 amino acids in length. Such a fragment may represent an epitope of the protein.

For example, one particularly desirable fragment of the invention is a T cell epitope located within a peptide of the invention, e.g., $IR_6$. Such a T cell epitope may be readily identified using available computer modelling programs.

Optionally, the peptides of the invention may be modified to create deletion mutants, for example, by truncation at the amino or carboxy termini, or by elimination of one or more amino acids. Still other modified fragments of $IR_{1-5}$ or $IR_6$ may be prepared by any number of now conventional techniques to improve production thereof, to enhance protein stability or other characteristics, e.g. binding activity or bioavailability, or to confer some other desired property upon the protein. Other useful fragments of these polypeptides may be readily prepared by one of skill in the art using known techniques, such as deletion mutagenesis and expression.

iii. Fusion or Multimeric Proteins and Compositions

The $IR_{1-5}$ or $IR_6$ peptides of the present invention, or fragments of it, may also be constructed, using conventional genetic engineering techniques as part of a larger and/or multimeric protein or protein compositions. In one currently preferred embodiment, a fusion protein is composed of an $IR_6$ fragment corresponding to a T cell epitope, which is fused to a peptide selected from among the $IR_{1-5}$ peptides of the invention.

The $IR_{1-5}$ and $IR_6$ peptides and proteins of this invention may be used in combination with *B. burgdorferi* outer surface proteins, such as OspA and OspB, or various fragments of these may be used in combination with each other. In such combination, the antigen may be in the form of a fusion protein. Thus, an antigen of the invention (e.g., $IR_6$ or a fragment thereof) may be optionally fused to a selected polypeptide or protein, e.g. Borrelia antigens OspA and OspB, other Borrelia antigens, and/or proteins or polypeptides derived from other microorganisms. For example, a peptide or polypeptide of this invention may be fused at its N-terminus or C-terminus to OspA polypeptide, or OspB polypeptide or to a non-OspA non-OspB polypeptide or combinations thereof. OspA and OspB polypeptides which may be useful for this purpose include polypeptides identified by the prior art [see, e.g. PCT/US91/04056] and variants thereof. Non-OspA, non-OspB polypeptides which may be useful for this purpose include polypeptides of the invention and those identified by the prior art, including, the *B. burgdorferi*, flagella-associated protein and fragments thereof, other *B. burgdorferi* proteins and fragments thereof, and non-*B. burgdorferi* proteins and fragments thereof.

These fusion proteins are constructed for use in the methods and compositions of this invention. These fusion proteins or multimeric proteins may be produced recombinantly, or may be synthesized chemically. They also may include the peptides and proteins of this invention fused or coupled to moieties other than amino acids, including lipids and carbohydrates. Further, antigens of this invention may be employed in combination with other Borrelia vaccinal agents described by the prior art, as well as with other species of vaccinal agents derived from other viruses. Such protein are effective in the prevention, treatment and diagnosis of Lyme disease as caused by a wide spectrum of *B. burgdorferi* isolates.

A protein composition which may be a preferred alternative to the fusion proteins described above is a cocktail (i.e., a simple mixture) containing an $IR_6$ peptides or protein, or different mixtures of the $IR_{1-5}$ and $IR_6$ peptides and proteins of this invention.

In still another aspect, the peptide and proteins of the invention may be provided with a detectable label, such as are described in detail below.

iv. Salts

A peptide or protein antigen of the present invention may also be used in the form of a pharmaceutically acceptable salt. Suitable acids and bases which are capable of forming salts with the polypeptides of the present invention are well known to those of skill in the art, and include inorganic and organic acids and bases.

B. Nucleic Acid Sequences

The present invention provides mammalian nucleic acid sequences encoding the $IR_{1-5}$ and $IR_6$ peptides and proteins of the invention, as defined above. Also provided are nucleic acid sequences complementary to the coding strand, e.g., the anti-sense strand, and corresponding RNA sequences.

Allelic variants of these sequences within a species (i.e., sequences containing some individual nucleotide differences from a more commonly occurring sequence within a species, but which nevertheless encode the same protein or a protein with the same function) may also be readily obtained given the knowledge of the nucleic acid sequence provided by this invention (see, FIG. 2).

The present invention further encompasses nucleic acid sequences capable of hybridizing under stringent conditions [see, J. Sambrook et al., *Molecular Cloning: A Laboratory Manual,* 2d ed, Cold Spring Harbor Laboratory (1989)] to the sequences of the invention, their anti-sense strands, or biologically active fragments thereof. An example of a highly stringent hybridization condition is hybridization at 2XSSC at 65° C., followed by a washing in 0.1XSSC at 65° C. for an hour. Alternatively, an exemplary highly stringent hybridization condition is in 50% formamide, 4XSSC at 42° C. Moderately high stringency conditions may also prove useful, e.g., hybridization in 4XSSC at 55° C., following by washing in 0.1XSSC at 37° C. for an hour. An alternative exemplary moderately high stringency hybridization condition is in 50% formamide, 4XSSC at 30° C.

According to the invention, the nucleic acid sequences may be modified. Utilizing the sequence data provided herein, it is within the skill of the art to obtain or prepare synthetically or recombinantly other polynucleotide sequences, or modified polynucleotide sequences, encoding the full-length proteins or useful fragments of the invention. Such modifications at the nucleic acid level include, for example, modifications to the nucleotide sequences which are silent or which change the amino acids, e.g., to improve expression or secretion. Also included are allelic variations, caused by the natural degeneracy of the genetic code.

Also encompassed by the present invention are mutants of the $IR_{1-5}$ and $IR_6$ peptides and proteins provided herein. Such mutants include amino terminal, carboxy terminal or internal deletions, which substantially retain the antigenicity of the full-length $IR_{1-5}$ and $IR_6$ or other proteins or fragments. Such a truncated, or deletion mutant may be expressed for the purpose of affecting the activity of the full-length or wild-type gene or gene fragments.

Thus, the invention provides fragments that grade a desirable fragment of $IR_{1-5}$ or $IR_6$, e.g., a T cell epitope. Generally, these olignoucleotide fragments are at least 15 nucleotides in length. However, oligonucleotide fragments of varying sizes may be selected as desired. Such fragments may be used for such purposes as performing polymerase chain reaction (PCR), e.g., on a biopsied tissue sample.

The nucleic acid sequences of the invention may be obtained, in whole or in part, from natural sources and isolated from the cellular materials with which they are naturally associated. For example, the sequences encoding $IR_{1-5}$ and $IR_6$ were originally isolated from a fragment, designated 7-1, from *Borrelia garinii* strain IP90, inserted in pBluescript II plasmid, was transformed in *E. coli* and deposited with the American Type Culture Collection, Manassas, Va. ("ATCC") on Jun. 27, 1997 under Accession No. 98478. 7-1 is described in detail in WO 99/00413, published Jan. 7, 1999, and incorporated herein by reference. However, the sequences of the invention may be isolated from other suitable sources by conventional uses of polymerase chain reaction or cloning techniques such as those described in conventional texts such as Sambrook et al, cited above.

More desirably, these nucleic acid sequences of the invention may be constructed recombinantly using conventional genetic engineering or chemical synthesis techniques or PCR, and the like by utilizing the information provided herein.

These nucleic acid sequences are useful for a variety of diagnostic, prophylactic and therapeutic uses. Advantageously, the nucleic acid sequences are useful in the development of diagnostic probes and antisense probes for use in the detection and diagnosis of Lyme disease by utilizing a variety of known nucleic acid assays, e.g., Northern and Southern blots, polymerase chain reaction (PCR) and other assay techniques known to one of skill in the art. When used in diagnostic applications, the nucleic acid sequences of the invention may optionally be associated with a detectable label, such as are described in detail below. The nucleic acid sequences of this invention are also useful in the production of the peptides and proteins of the invention.

II. Methods of Making Antigens and Nucleic Acid Sequences of the Invention

A. Expression In Vitro

To produce the recombinant $IR_{1-5}$ and $IR_6$ peptides and proteins of the invention, the DNA sequences of the invention are inserted into a suitable expression system. Desirably, a recombinant molecule or vector is constructed in which the polynucleotide sequence encoding the selected protein, e.g., an $IR_6$ peptide or protein, is operably liked to a heterologous expression control sequence permitting expression of the protein. Numerous types of appropriate expression vectors are known in the art for protein expression, by standard molecular biology techniques. Such vectors are selected from among conventional vector types including insects, e.g., baculovirus expression, or yeast, fungal, bacterial or viral expression systems. Other appropriate expression vectors, of which numerous types are known in the art, can also be used for this purpose. Methods for obtaining such expression vectors are well-known. See, Sambrook et al, *Molecular Cloning, A Laboratory Manual*, 2d edition, Cold Spring Harbor Laboratory, New York (1989); Miller et al, *Genetic Engineering*, 8:277–298 (Plenum Press 1986) and references cited therein.

Suitable host cells or cell lines for transfection by this method include bacterial cells. For example, the various strains of *E. coli* (e.g., HB101, MC1061, and strains used in the following examples) are well-known as host cells in the field of biotechnology. Various strains of *B. subtilis, Pseudomonas, Streptomyces,* and other bacilli and the like are also be employed in this method.

Mammalian cells, such as human 293 cells, Chinese hamster ovary cells (CHO), the monkey COS-1 cell line or murine 3T3 cells derived from Swiss, Balb-c or NIH mice are used. Another suitable mammalian cell line is the CV-1 cell line. Still other suitable mammalian host cells, as well as methods for transfection, culture, amplification, screening, production, and purification are known in the art. [See, e.g., Gething and Sambrook, *Nature*, 293:620–625 (1981), or alternatively, Kaufman et al, *Mol. Cell. Biol.*, 5(7):1750–1759 (1985) or Howley et al, U.S. Pat. No. 4,419,446].

Many strains of yeast cells known to those skilled in the art are also available as host cells for expression of the polypeptides of the present invention. Other fungal cells may also be employed as expression systems. Alternatively, insect cells such as *Spodoptera frugipedera* (Sf9) cells may be used.

Thus, the present invention provides a method for producing a recombinant $IR_{1-5}$ or $IR_6$ peptide or protein, which involves transfecting, e.g., by conventional means such as electroporation, a host cell with at least one expression vector containing a polynucleotide of the invention under the control of a transcriptional regulatory sequence. The transfected or transformed host cell is then cultured under conditions that allow expression of the protein. The expressed protein is recovered, isolated, and optionally purified from the cell (or from the culture medium, if expressed extracellularly) by appropriate means known to one of skill in the art.

For example, the proteins are isolated in soluble form following cell lysis, or extracted using known techniques, e.g., in guanidine chloride. If desired, the proteins or fragments of the invention are produced as a fusion protein. Such fusion proteins are those described above. Alternatively, for example, it may be desirable to produce fusion proteins to enhance expression of the protein in a selected host cell, to improve purification, or for use in monitoring the presence of the desired peptide or protein, e.g., $IR_6$, in tissues, cells or cell extracts. Suitable fusion partners for the peptides and proteins of the invention are well known to those of skill in the art and include, among others, β-galactosidase, glutathione-S-transferase, and polyhistidine.

B. Expression In Vivo

Alternatively, where it is desired that the $IR_{1-5}$ or $IR_6$ peptide or protein of the invention be expressed in vivo, e.g., to induce antibodies, or as a DNA vaccine, an appropriate vector for delivery is readily selected by one of skill in the art. Exemplary vectors for in vivo gene delivery are readily available from a variety of academic and commercial sources, and include, e.g., adeno-associated virus [International patent application No. PCT/US91/03440], adenovirus vectors [M. Kay et al, *Proc. Natl. Acad. Sci. USA*, 91:2353 (1994); S. Ishibashi et al., *J. Clin. Invest.*, 92:883 (1993)], or other viral vectors, e.g., various poxviruses, vaccinia, etc. Methods for insertion of a desired coding sequence, e.g., the sequence encoding the $IR_6$ peptide, and obtaining in vivo expression of the encoded protein, are well known to those of skill in the art.

III. Antibodies of the Invention

The present invention also provides antibodies capable of recognizing and binding the $IR_{1-5}$ and $IR_6$ peptides of this invention, including antibodies derived from mixtures of such antigens or fragments thereof. These antibodies are useful in diagnosis of Lyme disease and in therapeutic compositions for treating humans and/or animals that test positive for, or, prior to testing, exhibit symptoms of, Lyme Disease. The antibodies are useful in diagnosis alone (e.g., those antibodies raised using $IR_6$ peptides and proteins) or in combination with antibodies to other antigens of this invention as well as antibodies to other known B. burgdorferi antigens. These antibodies particularly those generated using $IR_{1-5}$, are also useful in passive vaccine compositions.

The antibodies of this invention are generated by conventional means utilizing the isolated, recombinant or modified antigens of this invention, or mixtures of such antigens or antigenic fragments. For example, polyclonal antibodies are generated by conventionally stimulating the immune system of a selected animal or human with the isolated antigen or mixture of antigenic proteins or peptides of this invention, allowing the immune system to produce natural antibodies thereto, and collecting these antibodies from the animal or human's blood or other biological fluid.

Monoclonal antibodies (MAbs) directed against an $IR_{1-5}$ or $IR_6$ peptide or protein of the invention may also be generated. Hybridoma cell lines expressing desirable MAbs are generated by well-known conventional techniques, e.g. Kohler and Milstein and the many known modifications thereof. Similarly desirable high titer antibodies are generated by applying known recombinant techniques to the monoclonal or polyclonal antibodies developed to these antigens [see, e.g., PCT Patent Application No. PCT/GB85/00392; British Patent Application Publication No. GB2188638A; Amit et al., *Science*, 233:747–753 (1986); Queen et al., *Proc. Nat'l. Acad. Sci. USA*, 86:10029–10033 (1989); PCT Patent Application No. PCT/WO9007861; and Riechmann et al., *Nature*, 332:323–327 (1988); Huse et al., *Science*, 246:1275–1281 (1988)a].

Given the disclosure contained herein, one of skill in the art may generate chimeric, humanized or fully human antibodies directed against an $IR_{1-5}$ or $IR_6$ peptide or protein of the invention by resort to known techniques by manipulating the complementarity determining regions of animal or human antibodies to the antigen of this invention. See, e.g., E. Mark or Padlin, "Humanization of Monoclonal Antibodies", Chapter 4, *The Handbook of Experimental Pharmacology*, Vol. 113, The Pharmacology of Monoclonal Antibodies, Springer-Verlag (June, 1994).

Alternatively, the antigens may be assembled as multi-antigenic complexes [see, e.g., European Patent Application 0339695, published Nov. 2, 1989] or as simple mixtures of antigenic proteins/peptides and employed to elicit high titer antibodies capable of binding the selected antigen(s) as it appears in the biological fluids of an infected animal or human.

Further provided by the present invention are anti-idiotype antibodies (Ab2) and anti-anti-idiotype antibodies (Ab3). Ab2 are specific for the target to which anti-$IR_{1-5}$ or anti-$IR_6$ antibodies (Ab1) of the invention bind and Ab3 are similar to Ab1 in their binding specificities and biological activities [see, e.g., M. Wettendorff et al., "Modulation of anti-tumor immunity by anti-idiotypic antibodies." In *Idiotypic Network and Diseases*, ed. by J. Cerny and J. Hiernaux J, Am. Soc. Microbiol, Washington DC: pp. 203–229, (1990)]. These anti-idiotype and anti-anti-idiotype antibodies are produced using techniques well known to those of skill in the art. Such anti-idiotype antibodies (Ab2) can bear the internal image of the antigens, and are thus useful for the same purposes as the $IR_{1-5}$ and $IR_6$ peptides and proteins of the invention.

In general, polyclonal antisera, monoclonal antibodies and other antibodies which bind to the selected antigen (Ab1) are useful to identify epitopes of $IR_{1-5}$ and $IR_6$ and to separate these peptides and proteins from contaminants in tissue (e.g., in chromatographic columns and the like), and in general as research tools and as starting materials essential for the development of other types of antibodies described above. Anti-idiotype antibodies (Ab2) are useful for binding the same target and thus may be used in place of the original antigen.

For use in diagnostic assays, the antibodies are associated with conventional labels which are capable, alone or in concert with other compositions or compounds, of providing a detectable signal. Where more than one antibody is employed in a diagnostic method, the labels are desirably interactive to produce a detectable signal. Most desirably, the label is detectable visually, e.g. colorimetrically. A variety of enzyme systems have been described in the art which will operate to reveal a colorimetric signal in an assay. As one example, glucose oxidase (which uses glucose as a substrate) releases peroxide as a product. Peroxidase, which reacts with peroxide and a hydrogen donor such as tetramethyl benzidine (TMB), produces an oxidized TMB that is seen as a blue color. Other examples include horseradish peroxidase (HRP) or alkaline phosphatase (AP), and hexokinase in conjunction with glucose-6-phosphate dehydrogenase which reacts with ATP, glucose, and NAD+ to yield, among other products, NADH that is detected as increased absorbance at 340 nm wavelength. Other label systems that may be utilized in the methods of this invention are detectable by other means, e.g., colored latex microparticles [Bangs Laboratories, Ind.] in which a dye is embedded may be used in place of enzymes to form conjugates with the antibodies and provide a visual signal indicative of the presence of the resulting complex in applicable assays. Still other labels include fluorescent compounds, radioactive compounds or elements. Detectable labels for attachment to antibodies useful in diagnostic assays of this invention may be easily selected from among numerous compositions known and readily available to one skilled in the art of diagnostic assays. The methods and antibodies of this invention are not limited by the particular detectable label or label system employed. Suitably, these detectable systems may also be utilized in connection with diagnostic reagents composed of the peptides, proteins, and nucleic acid sequences of the invention.

IV. Diagnostic Methods and Assays

The present invention provides reliable and accurate methods of diagnosing Lyme disease. These diagnostic methods are useful for diagnosing humans or animals exhibiting the clinical symptoms of, or suspected of having, Lyme disease. The $IR_6$ peptides, proteins and nucleic acids of the invention are particularly well suited for use in the diagnostic methods and compositions of the invention and for convenience reference will be made to $IR_6$ throughout this and the following section. However, it will be understood that, although less desirable, the $IR_{1-5}$ peptides, proteins and nucleic acids may be useful in these methods.

In one embodiment, this diagnostic method involves detecting the presence of naturally occurring *B. Burgdorferi* antibodies which are produced by the infected human or animal patient's immune system in its biological fluids, and which are capable of binding to the antigens of this invention or combinations thereof. This method comprises the steps of incubating an $IR_6$ peptide or protein of this invention with a sample of biological fluids from the patient. Antibodies present in the fluids as a result of *B. burgdorferi* infection will form an antibody-antigen complex with the antigen. Subsequently the reaction mixture is analyzed to determine the presence or absence of these antigen-antibody complexes. The step of analyzing the reaction mixture comprises contacting the reaction mixture with a labeled specific binding partner for the antibody.

In one embodiment of the method, the $IR_6$ peptide or protein, or a mixture of the peptides and proteins of the invention is electro- or dot-blotted onto nitrocellulose paper. Subsequently, the biological fluid (e.g. serum or plasma) is incubated with the blotted antigen, and antibody in the biological fluid is allowed to bind to the antigen(s). The bound antibody is then detected by standard immunoenzymatic methods.

In another embodiment of the method, latex beads are conjugated to the antigen(s) of this invention. Subsequently, the biological fluid is incubated with the bead/protein conjugate, thereby forming a reaction mixture. The reaction mixture is then analyzed to determine the presence of the antibodies.

In another embodiment, the diagnostic method of the invention involves detecting the presence of the naturally occurring $IR_6$ antigen(s) itself in its association with the *B. burgdorferi* pathogen in the biological fluids of an animal or human infected by the pathogen. This method includes the steps of incubating an antibody of this invention (e.g., produced by administering to a suitable human and/or animal an antigen of this invention), preferably conventionally labelled for detection, with a sample of biological fluids from a human or an animal to be diagnosed. In the presence of *B. burgdorferi* infection of the human or animal patient, an antigen-antibody complex is formed (specific binding occurs). Subsequently, excess labeled antibody is optionally removed, and the reaction mixture is analyzed to determine the presence or absence of the antigen-antibody complex and the amount of label associated therewith.

Assays employing a protein antigen of the invention can be heterogenous (i.e., requiring a separation step) or homogenous. If the assay is heterogenous, a variety of separation means can be employed, including centrifugation, filtration, chromatography, or magnetism.

One preferred assay for the screening of blood products or other physiological or biological fluids is an enzyme linked immunosorbant assay, i.e., an ELISA. Typically in an ELISA, the isolated antigen(s) of the invention is adsorbed to the surface of a microtiter well directly or through a capture matrix (i.e., antibody). Residual protein-binding sites on the surface are then blocked with an appropriate agent, such as bovine serum albumin (BSA), heat-inactivated normal goat serum (NGS), or BLOTTO (a buffered solution of nonfact dry milk which also contains a preservative, salts, and an antifoaming agent). The well is then incubated with a biological sample suspected of containing specific anti-*B. burgdorferi* antibody. The sample can be applied neat, or more often, it can be diluted, usually in a buffered solution which contains a small amount (0.1–5.0% by weight) of protein, such as BSA, NGS, or BLOTTO. After incubating for a sufficient length of time to allow specific binding to occur, the well is washed to remove unbound protein and then incubated with labeled anti-human immunoglobulin (α HuIg) or labeled antibodies to other species, e.g., dogs. The label can be chosen from a variety of enzymes, including horseradish peroxidase (HRP), β-galactosidase, alkaline phosphatase, and glucose oxidase, as described above. Sufficient time is allowed for specific binding to occur again, then the well is washed again to remove unbound conjugate, and the substrate for the enzyme is added. Color is allowed to develop and the optical density of the contents of the well is determined visually or instrumentally.

In one currently preferred embodiment, the invention provides a modified ELISA which has been found to have an overall sensitivity of 90%, with a specificity of about 99%, a positive predictive value of about 99% and a negative predictive value of about 89%. Thus, the ELISA of the invention is performed in a ninety-six-well ELISA plate or equivalent solid phase coated with streptavidin or an equivalent biotin-binding compound at an optimal concentration in an alkaline coating buffer and incubated at 4° C. overnight. After two 3-min washes with standard washing buffers such as 10 mM sodium phosphate, 150 mM NaCl and 0.1% Tween-20, pH 7.4 (PBST), an optimal concentration of a biotinylated form of a composition/antigen of this invention dissolved in a conventional blocking buffer such as PBST supplemented with 5% nonfat dry milk, is applied to each well. After 2 hours of incubation with shaking and three washes as above, a sample of biological fluids at the appropriate dilution, obtained from a human or an animal to be diagnosed, is added to each well. The plate is incubated with shaking for 1 hour at RT and then washed as before. Each well then receives an optimal concentration of an appropriate anti-immunoglobulin antibody that is conjugated to an enzyme or other label by standard procedures and is dissolved in blocking buffer. After one additional hour of incubation followed by four washes with PBST for 3, 4, 5 and 6 minutes, respectively, a solution composed of an appropriate chromogen or indicator is added and color is allowed to develop for 10 minutes. The enzyme reaction is appropriately stopped and optical density is measured at the appropriate wave length. The cutoff OD value may be defined as the mean OD+3 standard deviations (SDs) of at least 50 serum samples collected from individuals from an area where Lyme disease is not endemic, or by other such conventional definitions.

Further, MAbs or other antibodies of this invention which are capable of binding to the antigen(s) can be bound to ELISA plates. In another diagnostic method, the biological fluid is incubated on the antibody-bound plate and washed. Detection of any antigen-antibody complex, and equalitative measurement of the labeled MAb is performed conventionally, as described above.

Other useful assay formats include the filter cup and dipstick. In the former assay, an antibody of this invention is fixed to a sintered glass filter to the opening of a small cap. The biological fluid or sample (5 mL) is worked through the filter. If the antigen is present (i.e., *B. burgdorferi* infection), it will bind to the filter which is then visualized through a second antibody/detector. The dipstick assay involves fixing an antigen or antibody to a filter, which is then dipped in the biological fluid, dried and screened with a detector molecule.

Other diagnostic assays can employ the antigen(s) or fragments of this invention as nucleic acid probes or as anti-sense sequences, which can identify the presence of infection in the biological fluid by hybridizing to complementary sequences produced by the pathogen in the biological fluids. Such techniques, such as PCR, Northern or Southern hybridizations etc. are well known in the art.

It should be understood by one of skill in the art that any number of conventional protein assay formats, particularly immunoassay formats, or nucleic acid assay formats, may be designed to utilize the isolated antigens and antibodies or their nucleic acid sequences or anti-sense sequences of this invention for the detection of *B. burgdorferi* infection in animals and humans. This invention is thus not limited by the selection of the particular assay format, and is believed to encompass assay formats which are known to those of skill in the art.

V. Diagnostic Kits

For convenience, reagents for ELISA or other assays according to this invention may be provided in the form of kits. Such kits are useful for diagnosing infection with *B. burgdorferi* in a human or an animal sample. Such a diagnostic kit contains an antigen of this invention and/or at least one antibody capable of binding an antigen of this invention, or the nucleic acid sequences encoding them, or their anti-sense sequences. Alternatively, such kits may contain a simple mixture of such antigens or sequences, or means for preparing a simple mixture.

These kits can include microtiter plates to which the $IR_{1-5}$ or $IR_6$ peptides, proteins, antibodies, or nucleic acid sequences of the invention have been pre-adsorbed, various diluents and buffers, labeled conjugates for the detection of specifically bound antigens or antibodies, or nucleic acids and other signal-generating reagents, such as enzyme substrates, cofactors and chromogens. Other components of these kits can easily be determined by one of skill in the art. Such components may include polyclonal or monoclonal capture antibodies, antigen of this invention, or a cocktail of two or more of the antibodies, purified or semi-purified extracts of these antigens as standards, MAb detector antibodies, an anti-mouse or anti-human antibody with indicator molecule conjugated thereto, an ELISA plate prepared for absorption, indicator charts for colorimetric comparisons, disposable gloves, decontamination instructions, applicator sticks or containers, and a sample preparator cup. Such kits provide a convenient, efficient way for a clinical laboratory to diagnose *B. burgdorferi* infection.

VI. Therapeutic Compositions

The antigens, antibodies, nucleic acid sequences or anti-sense sequences of the invention, alone or i combination with other antigens, antibodies, nucleic acid sequences or anti-sense sequences may further be used in therapeutic compositions and in methods for treating humans and/or animals with Lyme Disease. For example, one such therapeutic composition may be formulated to contain a carrier or diluent and one or more of the antibodies of the invention. Suitable pharmaceutically acceptable carriers facilitate administration of the proteins but are physiologically inert and/or nonharmful.

Carriers maybe selected by one of skill in the art. Exemplary carriers include sterile saline, lactose, sucrose, calcium phosphate, gelatin, dextran, agar, pectin, peanut oil, olive oil, sesame oil, and water. Additionally, the carrier or diluent may include a time delay material, such as glycerol monostearate or glycerol distearate alone or with a wax. In addition, slow release polymer formulations can be used.

Optionally, this composition may also contain conventional pharmaceutical ingredients, such as preservatives, or chemical stabilizers. Suitable ingredients which may be used in a therapeutic composition in conjunction with the antibodies include, for example, casamino acids, sucrose, gelatin, phenol red, N-Z amine, monopotassium diphosphate, lactose, lactalbumin hydrolysate, and dried milk.

Alternatively, or in addition to the antibodies of the invention, other agents useful in treating Lyme disease, e.g., antibiotics or immunostimulatory agents and cytokine regulation elements, are expected to be useful in reducing or eliminating disease symptoms. Agents which can be used to suppress or counteract the immune suppressants released by the tick vector or the spirochete should act to assist the natural immunity of the infected human or animal. Thus, such agents may operate in concert with the therapeutic compositions of this invention. The development of therapeutic compositions containing these agents is within the skill of one in the art in view of the teachings of this invention.

According to the method of the invention, a human or an animal may be treated for Lyme Disease by administering an effective amount of such a therapeutic composition. An "effective amount" may be between about 0.05 to about 1000 $\mu$g/mL of an antibody of the invention. A suitable dosage may be about 1.0 mL of such an effective amount. Such a composition may be administered 1–3 times per day over a 1 day to 12 week period. However, suitable dosage adjustments may be may be the attending physician or veterinarian depending upon the age, sex, weight and general health of the human or animal patient. Preferably, such a composition is administered parenterally, preferably intramuscularly or subcutaneously. However, it may also be formulated to be administered by any other suitable route, including orally or topically.

VII. Vaccine Compositions

The present invention provides a vaccine composition containing an $IR_{1-5}$ or $IR_6$ protein or peptide of the invention or mixtures thereof and a pharmaceutically acceptable carrier or diluent. In another embodiment, the invention provides a vaccine composition containing a nucleic acid sequence of the invention, or mixtures thereof, and a pharmaceutically acceptable carrier or diluent. Combinations of these antigen(s) of this invention with other antigens of *B. burgdorferi,* such a the OspA and OspB proteins, BmpA, B, C or D proteins, or fragments thereof are also encompassed by this invention.

Exemplary carriers are as described above for therapeutic compositions. Optionally, the vaccine composition may further contain adjuvants, preservatives, chemical stabilizers, or other antigenic proteins. Typically, stabilizers, adjuvants, and preservatives are optimized to determine the best formulation for efficacy in the target human or animal. Suitable exemplary preservatives include chlorobutanol, potassium sorbate, sorbic acid, sulfur dioxide, propyl gallade, the parabens, ethyl vanillin, glycerin, phenol, and parachlorophenol.

One or more of the above described vaccine components may be admixed or adsorbed with a conventional adjuvant. The adjuvant is used to attract leukocytes or enhance an immune response. Such adjuvants include, among others, Ribi, mineral oil and water, aluminum hydroxide, Amphigen, Avridine, L121/squalene, D-lactide-polylactide/glycoside, pluraonic plyois, muramyl dipeptide, killed Bordetella and saponins, such as Quil A. In addition, a vaccine composition of the invention may further comprise other, non-*B. burgdorferi* antigens, including, *Bordertella bronchiseptica,* canine parvovirus, canine distemper, rabies, Leptosporidia, canine coronavirus, and canine adenovirus. Other vaccinal antigens originating from other species may also be included in these compositions, e.g., feline coronavirus, etc.

The invention thus also encompasses a prophylactic method entailing administering to an animal or human an effective amount of such a composition. The vaccine compositions of the invention are administered in an "effective amount", that is, an amount of antigen that is effective in a route of administration to provide a vaccinal benefit, i.e., protective immunity. Suitable amounts of the antigen can be determine by one of skill in the art based upon the level of immune response desired. In general, however, a protein-based vaccine composition contains between 1 ng to 1000 mg antigen, and more preferably, 0.05 µg to 1 mg per L of antigen. Generally, a DNA-based vaccine contains a peptide or protein antigen of the invention optionally under the control of regulatory sequences. Where the antigen-encoding DNA is carried in a vector, e.g. a viral vector, a dose may be in the range of $1\times10^{-3}$ pfu to $1\times10^{12}$ pfu.

Other suitable does of the vaccine composition of the invention can be readily determined by one of skill in the art. Generally, a suitable dose is between 0.1 to 5 mL of the vaccine composition. In general, the vaccine will be administered once on a seasonal basis. Each tick season, usually in the spring, a booster should be administered. The vaccine may be administered by any suitable route. However, parenteral administration, particularly intramuscular, and subcutaneous, is the preferred route. Also preferred is the oral route of administration. Routes of administration may be combined, if desired, or adjusted. Further, depending upon the human patient or the animal species being treated, i.e., its weight, age, and general health, the dosage can also be determined readily by one of skill in the art.

VIII. Drug Screening and Development

The proteins, antibodies and polynucleotide sequences of the present invention may also be used in the screening and development of chemical compounds or proteins which have utility as therapeutic drugs or vaccines for the treatment or diagnosis or prevention of Lyme Disease. As one example, a compound capable of binding to $IR_{1-5}$ or $IR_6$ and preventing its biological activity may be a useful drug component for the treatment or prevention of Lyme Disease. The methods described herein may also be applied to fragments of $IR_{1-5}$ or $IR_6$, and, particularly, to epitopes within these fragments.

Suitable assay methods may be readily determined by one of skill in the art. Where desired, and depending on the assay selected, the selected antigen(s), e.g., $IR_6$, may be immobilized directly or indirectly (e.g., via an anti-$IR_6$ antibody) on a suitable surface, e.g., in an ELISA format. Such immobilization surfaces are well known. For example, a wettable inert bead may be used. Alternatively, the selected antigen, e.g., $IR_6$, may be used in screening assays which do not require immobilization, e.g., in the screening of combinatorial libraries. Assays and techniques exist for the screening and development of drugs capable of binding to an antigen of this invention, e.g., $IR_6$. These include the use of phage display system for expressing the antigenic protein(s), and using a culture of transfected *E. coli* or other microorganism to produce the proteins for binding studies of potential binding compounds. See, for example, the techniques described in G. Cesarini, *FEBS Letters*, 307(1):66–70 (July 1992); H. Gram et al., *J. Immunol. Meth.*, 161:169–176 (1993); C. Summer et al., *Proc. Natl. Acad. Sci., USA*, 89:3756–3760 (May 1992), incorporated by reference herein.

Other conventional drug screening techniques may be employed using the proteins, antibodies or polynucleotide sequences of this invention. As one example, a method for identifying compounds which specifically bind to a protein of this invention, e.g., $IR_6$, can include simply the steps of contacting a selected $IR_6$ protein with a test compound to permit binding of the test compound to $IR_6$, and determining the amount of test compound, if any, which is bound to the $IR_6$ protein. Such a method may involve the incubation of the test compound and the $IR_6$ protein immobilized on a solid support. Similar methods may be employed for one or more of the cassette string proteins.

Typically, the surface containing the immobilized ligand is permitted to come into contact with a solution containing the protein and binding is measured using an appropriate detection system. Suitable detection systems include the streptavidin horse radish peroxidase conjugate, direct conjugation by a tag, e.g., fluorescin. Other systems are well known to those of skill in the art. This invention is not limited by the detection system used.

Another method of identifying compounds which specifically bind to $IR_6$ or another peptide or protein of this invention can include the steps of contacting the peptide or protein, e.g., $IR_6$, immobilized on a solid support with both a test compound and the protein sequence which is a receptor for $IR_6$ to permit binding of the receptor to the $IR_6$ peptide or protein; and determining the amount of the receptor which is bound to the $IR_6$ peptide. The inhibition of binding of the normal protein by the test compound thereby indicates binding of the test compound to the $IR_6$ peptide. Similar methods may be employed for one or more of the cassette string proteins.

Thus, through use of such methods, the present invention is anticipated to provide compounds capable of interacting with $IR_6$ or portions thereof, and/or the $IR_{1-5}$ peptides or proteins and either enhancing or decreasing the protein's biological activity, as desired. Such compounds are believed to be encompassed by this invention.

The following examples illustrate the preferred methods for obtaining protein antigens of the invention and preparing the assays and compositions of the invention. Significantly, these examples indicate that the $IR_{1-5}$ and $IR_6$ peptides and proteins of this invention are useful for diagnosis and prophylaxis against Lyme disease and may improve Lyme serology. These examples are illustrative only and do not limit the scope of the invention.

EXAMPLE 1

Materials and Methods for Identification of $IR_{1-5}$ and $IR_6$ Peptides

A. Animals, Animal Infections and Spirochetal Strains

Rhesus monkeys (2 to 4-yr-old, *Macaca mulatta*) were infected by the bite of *Ixodes scapularis* nymphal ticks that were themselves infected either with *B. burgdorferi* sensu stricto strains JD1 or B31. Mice (6 to 8-wk-old C3H/HeN, Jackson Laboratories, Bar Harbor, Me.) were infected with *B. burgdorferi* sensu stricto strain Sh-2-82 (low passage, a gift from Denee Thomas, University of Texas Health Science Center, San Antonio, Tex.) by subcutaneous needle inoculation with $1\times10^8$ spirochetes administered in 1 ml of BSK-H medium (Sigma Chemical Co., St. Louis, Mo.), or by the bite of B31-infected *Ixodes scapularis* nymphal ticks. *B. garinii* strain IP90 (low passage) was obtained from the Centers for Disease Control and Prevention (CDC, Fort Collins, Colo.). When required, spirochetes were cultivated in BSK-H medium as described previously [Philipp, Infect. Immun., 61:3047–3059 (1993)].

B. Cloning, Sequencing and Expression of the 7-1 Cassette Segment of IP90

A library of randomly sheared total DNA from *B. garinii* IP90 was constructed in the λZAP II bacteriophage vector (Stratagene, La Jolla, Calif.) following a procedure described previously [R. Ramamoorthy et al, Infect. Immun., 64:1259–1264 (1996)]. The library was screened with a pool of plasma collected from rhesus monkeys within the first 10 wk after tick inoculation with B. burgdorferi JD1. On immunoblots of whole-cell extracts of B. garinii IP90 this plasma pool reacted strongly only with three components, namely flagellin, an unidentified 60-kDa protein, and an Ag which was the IP90 homolog of the 34 kDa VlsE of B31 [J. R. Zhang et al, Infect. Immun., 66:3698–3704 (1998)]. After several rounds of screening, eleven clones were rescued into the pBluescript phagemid (Stratagene). The recombinant plasmids were purified and used to transform cells of the SURE strain of E. coli (Stratagene). Several transformants were selected from each original clone, the presence of the insert was confirmed, and one such transformant from each clone was grown, induced for expression, lysed and analyzed by immunoblot analysis with the original plasma pool. One of the eleven cloned fragments (names 7-1) hybridized to all others by dot-blot hybridization. This fragment was selected for overexpression and purification on the basis of the strong reactivity of the expressed protein with the plasma Abs. Sequencing of the 7-1 insert was performed by standard procedures [J. Sambrook et al, Molecular cloning: A Laboratory Manual, Cold Spring Harbor Laboratory, Cold Spring Harbor, N.Y. (1989)] after generating Bal 31 nested deletions and subcloning the partially deleted fragments. Ab from the original plasma pool that was affinity purified using the recombinant protein (P7-1) expressed by clone 7-1 as immunoabsorbant reacted with the putative IP90 VlsE on immunoblot of B. garinii lysates. The 7-1 lysate was subcloned into the pQE expression system for overexpression and purification of the polypeptide (Qiagen Inc., Chatsworth, Calif). The protein concentration was determined using the Bio-Rad protein assay kit (Bio-Rad Laboratories, Richmond, Calif.) with BSA as a standard.

C. P7-1 ELISA

This protocol was initially used to monitor monkey Ab responses to P7-1. Ninety-six-well ELISA plates (Corning Inc., Corning, N.Y.) were coated with 100 µl per well of a solution of P7-1 at 0.1 µg/ml in coating buffer (0.1 M carbonate buffer, pH 9.2) at 4° C. overnight. Plates were blocked with 200 µl per well of 5% FCS in PBS/T (10 mM sodium phosphate, 150 mM NaCl and 0.1% Tween-20, pH 7.4) for 1 h at room temperature. After washing 3 times with PBS/T, 50 µl per well of serum samples from B. burgdorferi-infected monkeys diluted 1/100 in 5% FCS in PBS/T were incubated for 1 h at 37° C. Plates were washed and incubated with 50 µl of (1) a mixture of biotinylated goat anti-human IgG (γ-chain specific) and IgM (µ-chain specific) Abs at the dilution recommended by the manufacturer (Vector Laboratories, Inc., Burlingame, Calif.) for 1 h at 37° C., (2) avidin-horseradish peroxidase complex also at the dilution recommended by the manufacturer (Vector) for 30 min at 37° C., (3) a solution containing 2 g/l orthophenylenediamine and 0.03% hydrogen peroxide (both from Sigma) in 0.1 M citrate-sodium-phosphate buffer pH 5.0 for 10 min at room temperature. The reaction was stopped with 50 µl of 4 N $H_2SO_4$. OD at 490 nm was determined. Goat anti-human IgG and IgM fully crossreacted with monkey Ab.

D. Identification of Conserved Sequences and Prediction of Antigenicity of Invariable Regions of the VlsE Variable Domain The deduced amino acid sequence of P7-1 was compared with sequences available in the GenBank data base (National Center for Biotechnology Information, Rockville, Md.) using the BlastP algorithm [J. Zhang and T. L. Madden, Genome Res., 6:649–656 (1997)]. The antigenicity of the entire P7-1 polypeptide was analyzed using the Hopp-Woods scale [T. P. Hopp and K. R. Woods, Proc. Natl. Acad. Sci., USA, 78:3824–3828 (1981)], and identities of invariable regions of P7-1 with homologous cassette segments from strains B31 and 297 were calculated after aligning the cassette segments using the pam250 algorithm, and Mac Vector 5.0 computer software (Eastman Kodak Company, New Haven, Conn.).

E. Peptide Synthesis and Conjugation to Biotin

A 26-mer peptide ($C_6$) was prepared using the fluorenylmethoxycarbonyl synthesis protocol [G. Barony and R. B. Merrifield, The Peptides: Analysis, Synthesis, & Biology, Academic Press, pp. 3–285 (1980)]. A cysteine residue was included at the N-terminus and used as biotinylation site. Biotinylation was performed by the N-succinimidyl maleimide carboxylate method. The maleimide reagent was from Molecular Probes (Eugene, Oreg.) and the protocol suggested by the manufacturer was followed.

F. Human Serum Samples

A panel of 41 human serum samples was kindly provided by the CDC. All the samples were collected from Lyme disease patients who had signs and symptoms that satisfied the CDC clinical case definition [Morbidity and Mortality Weekly Report, 39, No. RR-13, 19–20 (1990)]. Four serum samples from chronic Lyme disease patients were obtained from the National Institutes of Health. Ninety-seven serum samples obtained from hospitalized patients in an area not endemic for Lyme disease were used as negative controls.

G. $C_6$ Peptide ELISA

Ninety-six-well ELISA plates were coated with 100 µl per well of 4 µg/ml streptavidin (Pierce Chemical Company, Rockford, Ill.) in coating buffer and incubated at 4° C. overnight. The remaining steps were conducted in a rotary shaker at room temperature. After two 3-min washes with 200 µl per well of PBS/T at 200 rpm, 200 µl of 5 µg/ml biotinylated peptide dissolved in blocking solution (PBS/T supplemented with 5% nonfat dry milk [Carnation, Nestle Food Company, Glendale, Calif.]) was applied to each well. The plate was shaken at 150 rpm for 2 h. After three washes with PBS/T as above, 50 µl of serum (mouse, monkey or human) diluted 1:200 with blocking solution was added to each well. The plate was incubated at 150 rpm for 1 h and then washed three times with PBS/T. Each well then received 100 µl of 0.2 µg/ml goat anti-monkey IgG (γ-chain specific, [Kirkegaard & Perry Laboratories, Gaithersburg, Md.]), 0.5 µg/ml anti-mouse IgG (heavy and light-chain specific, [Sigma]), or 0.1 µg/ml anti-human IgG (heavy and light-chain specific, [Pierce]), each conjugated to horseradish peroxidase and dissolved in blocking solution. The plate was incubated for 1 h while shaking. After four washes with PBS/T each for 3–6 min, the Ag-Ab reaction was probed using the TMB Microwell Peroxidase Substrate System (Kirkegaard & Perry), and color was allowed to develop for 10 min. The enzyme reaction was stopped by addition of 100 µl of 1 M $H_3PO_4$. OD was measured at 450 nm.

H. Competitive ELISA

Ninety-six-well ELISA plates were coated with 100 µl per well of 0.3 µg/ml of purified recombinant P7-1 dissolved in coating buffer at 4° C. overnight. After blocking with blocking solution, 25 µl of this solution with 0, 1, 4, 16, 64, 256 or 1024 ng of the $C_6$ peptide was added to each well. A 25-µl volume of a 1:100 dilution of the appropriate serum in blocking solution also was added to each well. The remaining steps were performed as related in the section describing the $C_6$ peptide ELISA.

I. Preparation of Rabbit Anti-$C_6$ Peptide Antiserum

The $C_6$ peptide was covalently linked to keyhole limpet hemocyanin (KLH) by the N-succinimidyl maleimide carboxylate method. The maleimide reagent was from Molecular Probes (Eugene) and the protocol suggested by the manufacturer was followed. Six-month-old New Zealand White rabbits were given three injections at bi-weekly intervals of 200 µg of conjugated Ag emulsified with Freund's complete (first injection) or incomplete adjuvant (remaining injections). Ten days after the last injection the Ab titer was determined by the peptide ELISA and immunoblot analysis using IP90 spirochete whole-cell lysates as Ag.

J. Immunoprecipitation and Immunoblot

Immunoprecipitation was conducted at 4° C. Approximately $1.5 \times 10^{10}$ IP90 spirochetes harvested at stationary growth phase were extracted in 4.5 ml solubilization buffer (50 mM Tris-HCl, 1% Triton X-100, 1 mM EDTA, pH 7.6) for 30 min. The mixture was centrifuged at 13,000× g for 30 min and the supernatant was collected. Each of 1.5 ml of this supernatant was mixed with 30 µl of preimmune or immune rabbit serum and incubated for 30 min. Fifty microliters of drained ImmunoPure™ Immobilized Protein G (Pierce) preequilibrated in solubilization buffer was then added and allowed to incubate for an additional 30 min. After washing the gel twice with excess volumes of this buffer by centrifugation at 3,000× g for 20 min, 150 µl of nonreducing SDS-PAGE sample buffer (125 mM Tris-HCl, 3% SDS and 20% glycerol, pH 6.8) was added. The suspension was incubated at room temperature for 30 min and then centrifuged at 16,000× g for 30 min. Ten microliters of supernatant was loaded onto each of the ten lanes of a SDS 12% polyacrylamide mini-gel. Separated proteins were electrotransferred to nitrocellulose in Towbin transfer buffer. After incubating in blocking solution for 2 h, the blot was incubated for 1 h in rabbit anti-$C_6$ serum diluted 1:2,000 with blocking solution. After 3 washes with PBS/T, the blot was incubated in blocking solution with 0.5 µg/ml goat anti-rabbit IgG conjugated to horseradish peroxidase (Pierce) for 1 h. The Ag-Ab reaction was probed in PBS/T supplemented with 0.05% 4-chloro-naphthol (Sigma), 0.015% hydrogen peroxide and 17% methanol.

K. Direct Immunofluorescence

Rabbit IgG was purified from preimmune or immune serum using conventional ammonium sulfate precipitation. The purity and concentration of IgG preparations were assessed using SDS-PAGE and the Bio-Rad protein assay kit, respectively. Purified IgG was conjugated to FITC as per the manufacturer's instruction (Pierce). For labeling, spirochetes were either unfixed or acetone fixed. For the fluorescent labeling of unfixed spirochetes, approximately 10 spirochetes that were harvested from 1.0 ml of IP90 culture grown to stationary phase by centrifugation at 4,000× g for 20 min were gently resuspended in 100 µl PBS supplemented with 2 µg rabbit anti-$C_6$ IgG-FITC conjugate, and incubated for 1 h. After 2 washes with excess volumes of PBS by centrifugation at 16,000× g for 5 min, spirochetes were resuspended in 100 µl PBS, applied to microscope slides and counted under both darkfield and fluorescent microscopes. The ratio of fluorescent to total spirochetes was thus calculated. The same procedure was performed on acetone fixed spirochetes. For this purpose, organisms harvested from 1.0 ml culture fluid were suspended in 1.5 ml acetone, incubated for 20 min, and then centrifuged at 16,000× g for 5 min. After one wash with PBS, the fixed spirochetes were stained with fluorescent anti-$C_6$ Ab as described for unfixed spirochetes. Goat anti-B. burgdorferi Ab FITC conjugate (Kirkegaard & Perry Laboratories) was used as positive control.

L. ADCK Assay

As a source of complement, serum samples were collected from normal rhesus macaques, pooled and stored in small aliquots at −70° C. until used. Serum chosen for this purpose did not contain cross-reactive anti-B. burgdorferi Abs as determined by immunoblot analysis using whole cell lysates of B. burgdorferi as Ag. To perform the ADCK assay, spirochetes were cultured in BSK-H medium until they reached mid-logarithmic phase (about $2 \times 10^7$ cells per ml). A total of approximately $5 \times 10^5$ spirochetes in 25 µl of BSK-H medium was added to each well of a 96-well plate (Corning Inc.). A volume of 50 µl of heat-inactivated (56° C., 30 min) serum sample appropriately diluted in the same medium was already dispensed in each well. The plate was incubated at 34° C. for 30 min before the addition of 25 µl of complement preparation (normal monkey serum). After 24 h of incubation at 34° C. in a humidified atmosphere of 3% $CO_2$, 5% $O_2$ and the balance of $N_2$, 5 µl of each sample was removed, and dead (nonmotile) and live (motile) spirochetes were counted under a darkfield microscope. Monkey anti-OspA antiserum was used as positive control [J. M. Nowling and M. T. Phillip, Infect. Immun., 67:443–445 (1999)].

EXAMPLE 2

The Invariable Regions of the VlsE Variable Domain are Conserved Among Strains and Genospecies of B. burgdorferi The Ab response to the recombinant P7-1 polypeptide in monkeys that had been tick inoculated with either B31 or JD1 B. burgdorferi spirochetes was assessed and it was noted that the response was detectable within the first three weeks post-infection (PI), and that it persisted at least until wk 10 PI, the longest time point measured in this initial experiment (FIG. 1). The deduced amino acid sequence of the B. garinii P7-1 recombinant polypeptide is shown in FIG. 2. It is depicted aligned with sequences from VlsE cassette segments of B. burgdorferi strains B31 [J. R. Zhang et al, Cell, 89:275–285 (1997)] and 297 [H. Kawabata et al, Microb. Pathog., 24:155–166 (1998)]. In B31, the cassette segment is comprised between the repeats EGAIKG [SEQ ID NO:2] (FIG. 2) [Zhang, cited above]. The six variable regions of the B31 VlsE cassette segment [Zhang, cited above] are doubly underlined. The invariable regions $IR_{1-6}$ of the IP90 VlsE variable domain (FIG. 2) are clearly conserved across both genospecies and strains of B. burgdorferi sensu lato. With the exception of $IR_1$, which is 78% conserved in strain B31 and only 11% in 297, all other invariable regions are between 80 and 90% conserved with respect to the P7-1 VlsE cassette segment of IP90 (Table 1).

TABLE 1

Identity between invariable regions from VlsE cassette segments of B. burgdorferi strains B31 and 297 and B. garinii IP90 (P7-1).

| | Percent Identity (%) | | |
|---|---|---|---|
| Invariable Region | B31 vs. IP90 | 297 vs. IP90 | Median |
| $IR_1$ | 78 | 11 | 45 |
| $IR_2$ | 81 | 88 | 85 |

TABLE 1-continued

Identity between invariable regions from VlsE cassette segments of B. burgdorferi strains B31 and 297 and B. garinii IP90 (P7-1).

| Invariable Region | Percent Identity (%) | | |
|---|---|---|---|
| | B31 vs. IP90 | 297 vs. IP90 | Median |
| $IR_3$ | 86 | 86 | 86 |
| $IR_4$ | 80 | 80 | 80 |
| $IR_5$ | 80 | 90 | 85 |
| $IR_6$ | 85 | 88 | 87 |

The antigenicity of the invariable regions of P7-1 was assessed with the Hopp-Woods hydrophilicity algorithm [Proc. Natl. Acad. Sci. USA, 78:3824–3828 (1981)]. Reputedly, this method has been more successful than similar ones for identifying protein antigenic determinants [T. P. Hopp, Pept. Res., 6:183–190 (1993)]. Overall, the invariable regions of the IP90 variable domain showed negative hydrophilicity values, possibly indicative of their lack of exposure on the surface of the protein. Sequences with positive values were composed of fewer than 6 amino acids and thus not likely to configure antigenic sites. In contrast, $IR_6$ contained six or more contiguous amino acids with relatively high positive hydrophilicity values (1.7). $IR_6$ was also slightly more conserved than other invariable regions, with a median identity of 87% when using the IP90 sequence as the reference strain (Table 1).

EXAMPLE 3

Experimental Assessment of the Antigenicity of $IR_6$

To evaluate experimentally the antigenicity of $IR_6$, the $C_6$ peptide, whose primary structure encompassed that of $IR_6$ with an added N-terminal cysteine reside for biotinylation, was synthesized as described in Example 1. The resulting $C_6$ peptide has the amino acid sequence: CMKKDDQIAAAM-VLRGMAKDGQFALK [SEQ ID NO:8].

Figure 3A:
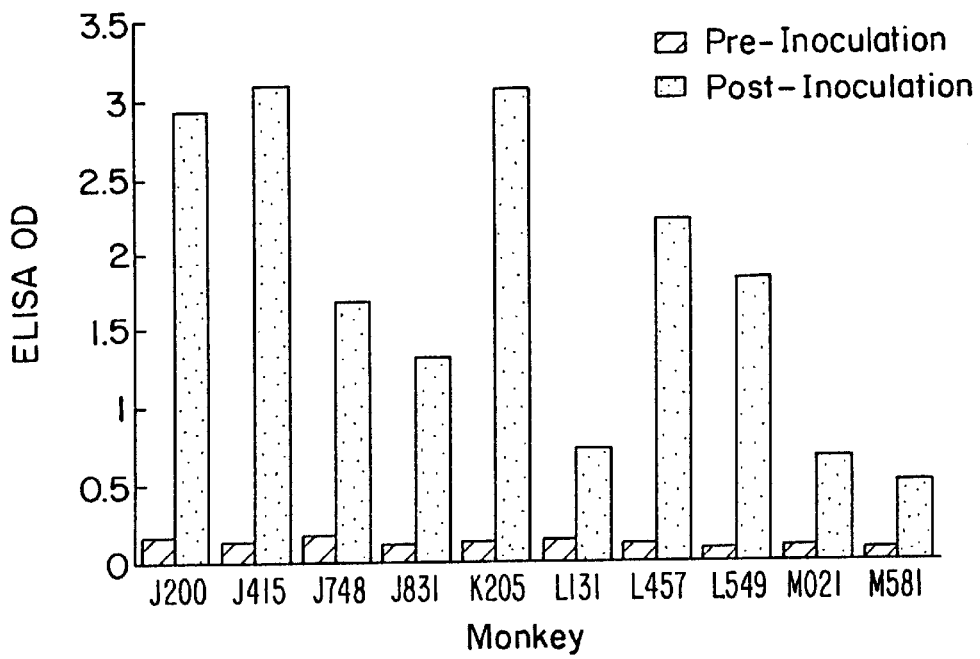
FIGS. 3A and 3B illustrate the antigenicity of $IR_6$ in monkeys (A) and mice (B). Serum samples were collected from monkeys or mice at 0 (pre and 4–6 wk PI (post). Animals were infected with the JD1 strain of *B. burgdorferi* (monkeys J200, J415, J748, J831, K205 and L131), the B31 strain (monkeys L457, L549, M021 and M581; mice 181, 191, 194 and 196), or the Sh-2-82 strain (mice 219, 220, 224, 288, 289 and 290). Ab levels were assessed by the $C_6$ ELISA.

Serum samples from bleeds obtained from 10 rhesus macaques that were infected either with JD1 (6 animals) or B31 spirochetes were used to examine the antigenicity of $IR_6$ in monkeys. Anti-$C_6$ ELISA Ab levels shown in FIG. 3A were present in serum samples at 4–6 wk PI and remained as high or higher for up to three years PI (data not shown).

Figure 3B:
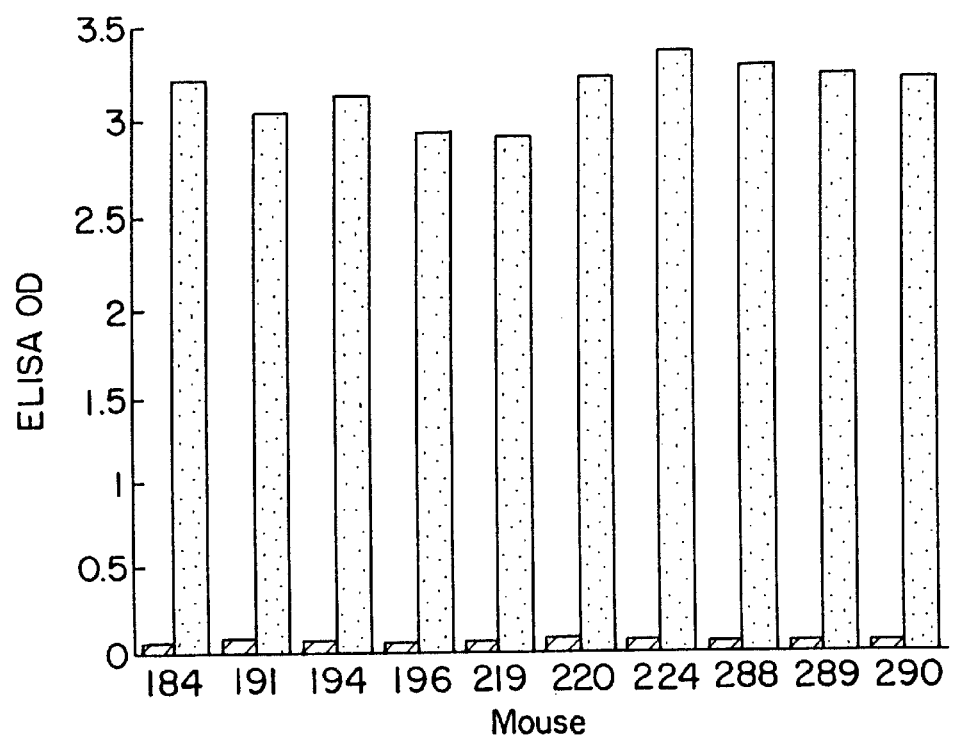

Mice also responded vigorously to this region. Serum samples collected 4–6 wk PI from 10 mice infected either with B. burgdorferi strain Sh-2-82 (6 animals) or B31 showed high levels of anti-$C_6$ Abs (FIG. 3B). This result further confirmed the antigenicity of $IR_6$ and reaffirmed this region's antigenic conservation.

In humans, the antigenicity of $IR_6$ was examined with the aid of the CDC panel of 41 serum samples. Ab directed to $C_6$ was found in 36 of the 41 samples (Table 2).

TABLE 2

Antigenicity of $IR_6$ in human patients whose signs and symptoms satisfied the CDC Lyme disease case definition.

| Serum ID# | $C_6$ ELISA OD | Serum ID# | $C_6$ ELISA OD |
|---|---|---|---|
| 90-2111 | P 3.055 | 91-1352 | P 1.763 |
| 90-2436 | P 2.541 | 91-1353 | P 0.550 |
| 90-2622 | P 3.099 | 91-1354 | P 1.140 |
| 90-2631 | N 0.276 | 91-1841 | P 0.607 |
| 90-2668 | P 1.625 | 91-1458 | P 1.056 |
| 91-0521 | P 1.423 | 91-1842 | P 1.423 |
| 91-0531 | P 3.330 | 91-1843 | P 1.733 |
| 91-0532 | P 1.942 | 91-1844 | P 1.879 |
| 91-0533 | P 2.178 | 91-1845 | N 0.222 |
| 91-0544 | P 3.091 | 91-1846 | N 0.338 |
| 91-0794 | P 0.600 | 91-1847 | P 1.676 |
| 91-0865 | P 3.274 | 92-0057 | P 1.735 |
| 91-0900 | P 2.386 | 92-1682 | N 0.404 |
| 91-0943 | P 2.959 | 92-1941 | N 0.432 |
| 91-1104 | P 1.642 | 92-1982 | P 0.832 |
| 91-1222 | P 2.274 | 93-0206 | P 0.633 |
| 91-1347 | P 0.960 | 93-0208 | P 0.600 |
| 91-1348 | P 3.233 | 93-1414 | P 1.025 |
| 91-1349 | N 0.448 | 93-1426 | P 0.832 |
| 91-1350 | P 1.246 | 94-0357 | P 0.739 |
| 91-1351 | P 0.843 | | |

N: negative result. P: positive result.

The result of this experiment also underscores both the antigenicity and antigenic conservation of $IR_6$, as the CDC serum panel was composed of samples collected from several Lyme disease endemic areas in the United States and must therefore encompass Abs to multiple strains of B. burgdorferi.

EXAMPLE 4

$IR_6$ is the Only Immunodominant Invariable Region in Both Monkeys and Humans

In addition to $IR_6$, the VlsE variable domain contains five other invariable regions (FIG. 2). To determine if any of these regions is antigenic, a competitive ELISA was performed, using P7-1 as Ag attached to an ELISA plate, in the presence of increasing concentrations of the $C_6$ peptide. P7-1 includes the invariable regions $IR_{1-6}$ (FIG. 2). Ten serum samples from infected monkeys, 4 human serum samples randomly selected from the CDC panel, and an additional 4 serum samples from chronic Lyme disease patients provided by the National Institutes of Health were tested. Representative results for 4 humans and 4 monkey serum samples are presented in FIG. 4. Addition of $C_6$ almost completely inhibited the reaction of monkey and human serum Abs reactive with P7-1. Thus $IR_6$ appears to be the only immunodominant invariable region within the VlsE variable domain in both monkeys and humans. When the competitive ELISA was used to analyze infected mouse serum, the maximum inhibition resulting from the addition of $C_6$ was no larger than 40%, indicating that other invariable regions may be antigenic in mice (data not shown).

EXAMPLE 5

Exposure of $IR_6$ on the Surface of VlsE

Figure 5:
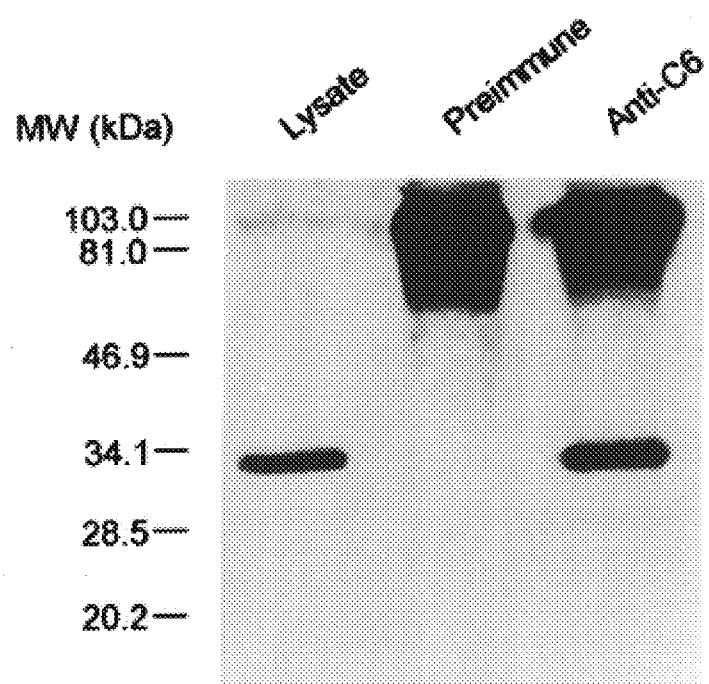
FIG. 5 demonstrates the exposure of $IR_6$ on the VlsE surface. VlsE from *B. garinii* strain IP90 spirochetes was extracted in solubilization buffer, and immunoprecipitated with protein G-agarose in the presence of rabbit anti-$C_6$ antiserum or preimmune serum. Solubilized immunoprecipitates and a whole-cell lysate of IP90 spirochetes were electrophoresed on a SDS-12%-polyacrylamide mini-gel and blotted onto nitrocellulose. VlsE was visualized with the anti-$C_6$ antiserum. Besides the VlsE band (low), single rabbit IgG bands (top) are visible since nonreducing SDS-PAGE sample buffer was used.

The exposure of $IR_6$ on the surface of the VlsE protein was examined by immunoprecipitation with the rabbit anti-$C_6$ antiserum. VlsE from IP90 spirochetes was extracted in solubilization buffer and precipitated with protein-G-agarose in the presence of either rabbit anti-$C_6$ antiserum or serum obtained from the same rabbit prior to immunization. Presence of VlsE in the immunoprecipitates was then assessed on immunoblots reacted with the anti-$C_6$ antiserum. The VlsE of IP90 was immunoprecipitable with the anti-$C_6$ antiserum but not with normal serum (FIG. 5). This result indicates that $IR_6$ is exposed on the VlsE surface.

EXAMPLE 6

IR$_6$ is Not Accessible to Ab on the Outer Membrane of the Spirochete

Figures 6A, 6B:
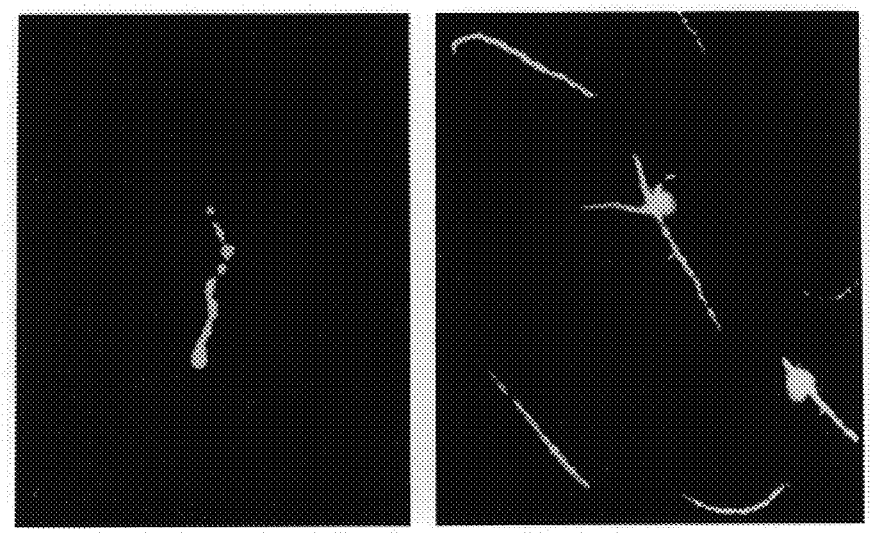
FIGS. 6A and 6B illustrate the lack of exposure of $IR_6$ on the spirochetal surface. *B. garinii* strain IP90 spirochetes were either left unfixed (A) or fixed with acetone (B), and labeled with rabbit anti-$C_6$ Ab conjugated to FITC.

Exposure of IR$_6$ on the spirochetal surface was assessed by immunofluorescence. While FITC-conjugated anti-C$_6$ Ab extensively labeled all of the acetone-fixed IP90 spirochetes (FIG. 6B), it labeled few (less than 5%) of the unfixed spirochetes (FIG. 6A). The unfixed spirochetes that were labeled exhibited a discontinuous fluorescent pattern, whereas fixed spirochetes fluoresced uniformly (FIG. 6). Control anti-B. burgdorferi Ab-FITC conjugate labeled both fixed and unfixed spirochetes (data not shown). These results indicate that IR$_6$ is constrained from the surface of the spirochete although the VlsE is surface-exposed [Zhang, Cell, 89:275–285 (1997)]. This is consistent with the observation made in our ADCK assay, in which anti-C$_6$ antiserum had no significant killing activity compared with preimmune serum although monkey anti-OspA antiserum killed all spirochetes in the same experiment (data not shown).

EXAMPLE 7

IR$_{1-5}$ and IR$_6$

It has been demonstrated that the amino acid sequences of the six invariable regions described previously in the cassette segments of VlsE [Zhang, cited above] are conserved, at least in two Borrelia genospecies, B. garinii and B. burgdorferi sensu stricto. Further, it has been illustrated with data from the literature that such conservation is also retained among strains of the latter genospecies. This is evident from the high level of identity between the deduced amino acid sequence of the invariable regions within the variable domain of IP90 (B. garinii), which we cloned, sequenced and identified ourselves, and those of the B31 and 297 cassette segments (FIG. 2, Table 1).

The sequence conservation of the six invariable regions across strain and genospecies barriers indicates that these regions are important in whichever role VlsE may play in the physiological of B. burgdorferi. One would therefore expect that such sequences are not antigenic in hosts with a chronic B. burgdorferi infection or would be otherwise accessible to Ab, either because they are conformationally buried within the VlsE molecule or unavailable on the spirochetal surface. The Hopp-Woods algorithm indicated that, with the exception of IR$_6$, all of the other invariable regions were either not antigenic or had very low antigenicity.

The predicted antigenicity of IR$_6$ was confirmed in humans, monkeys and mice (FIG. 3, Table 2). Sera from all of these hosts reacted with the C$_6$ peptide early and persistently in the course of infection, thus indicating that IR$_6$ contains one or more epitopes that may be broadly antigenic, regardless of host species. The antigenicity of C$_6$ was not only manifest independently of host species but also regardless of whether the animals had been infected with the JD1, B31 or Sh-2-82 strains of B. burgdorferi sensu stricto. In addition, 36 of 41 human serum samples collected in the Northeast and Midwest of the U. S. from patients with acute or chronic Lyme disease also reacted with this peptide. The 5 serum samples that had no detectable anti-C$_6$ Ab were obtained from patients who were in early stages of infection. Hence, the negative results may reflect presence of very low serum Ab titers rather than absence of crossreactivity. The C$_6$ peptide may thus serve as a global diagnostic probe.

Figure 4A:
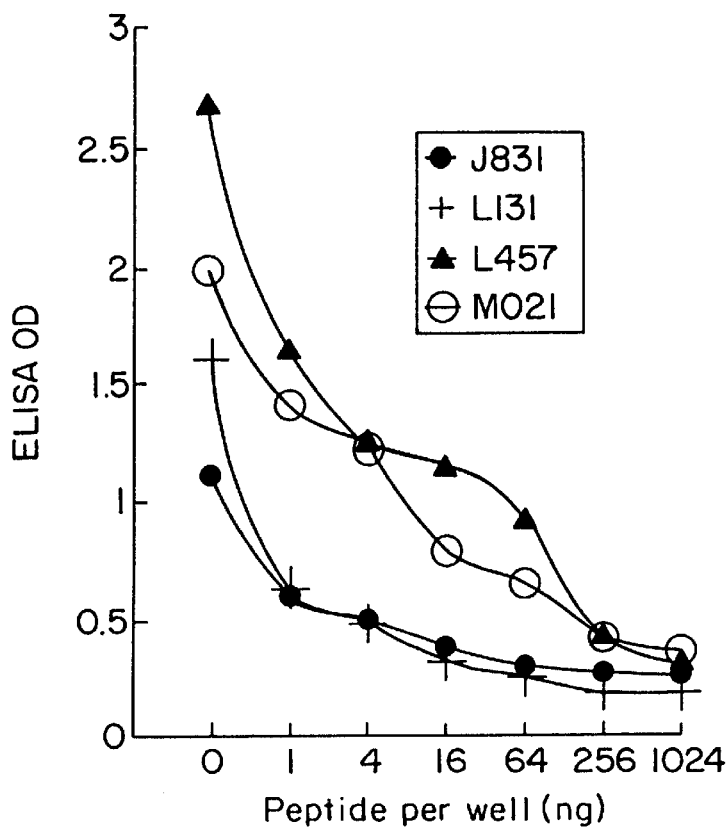
FIGS. 4A and 4B illustrate the immunodominance of $IR_6$ in monkeys and humans. Serum samples were obtained from (A) monkeys inoculated 4–6 wk PI with spirochetes of the JD1 strain of *B. burgdorferi* (J831 and L131) or the B31 strain (L457 and M021), and from (B) humans with an acute *B. burgdorferi* infection (91-1222 and 91-1348) or a chronic infection (91-0532 and 91-0533). Ab levels to P7-1 were assessed in the presence of increasing concentrations of the $C_6$ peptide by the competitive ELISA procedure.
Figure 4B:
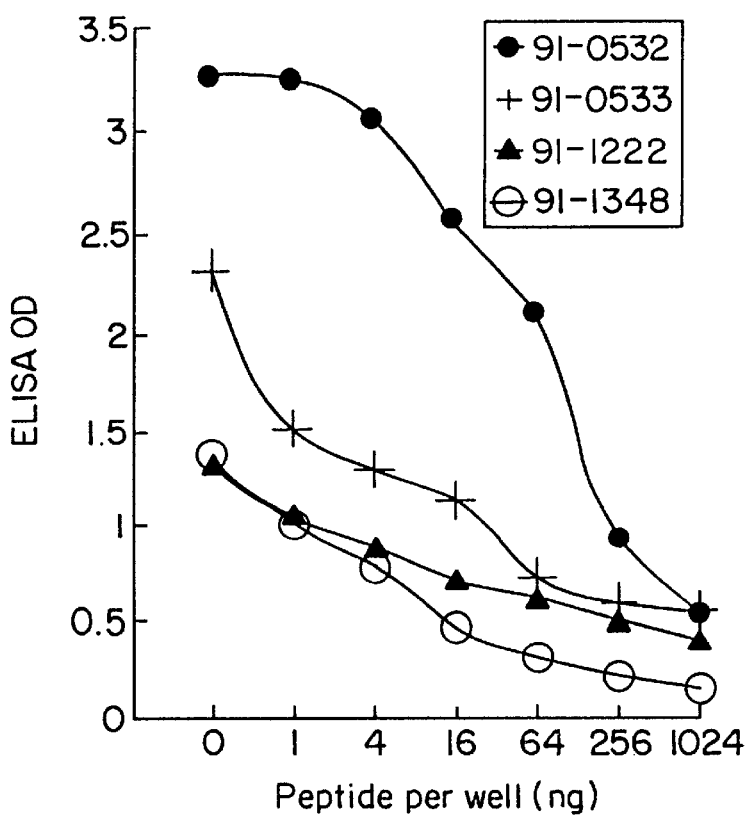

The absence of, or relatively low, antigenicity of IR$_{1-5}$ was underscored by the results of the competition experiments (FIG. 4). The fact that the binding of most of the human and monkey Ab that reacted with P7-1 could be inhibited simply by adding an excess of the C$_6$ peptide indicates that in these hosts IR$_6$ is possibly the only immunodominant invariable region within the VlsE variable domain. In mice the results were different, as we were unable to fully inhibit the P7-1 reactivity of mouse anti-Sh-2-82 or anti-B31 Abs with an added excess of the C$_6$ peptide. This result entails that some of the other invariable regions may be antigenic in mice. The immunodominance of IR$_6$ was further underscored by the long-term persistence of anti-C$_6$ Abs in infected monkeys and in patients with chronic Lyme disease (data not shown).

The Hopp-Woods algorithm also predicted, as expected, that some variable regions of the cassette segment are strongly antigenic (data not shown). Thus, at least theoretically, the VlsE variable regions could satisfy the antigenic variations paradigm that variable domains are immunodominant. In the case of VlsE, however, variable region immunodominance of individual VlsE molecules may be difficult to achieve, for the recombination process that underlies the mechanism of VlsE variation occurs very rapidly [J. R. Zhang et al, Infec. Immun., 66:3869–3697)]. In spite of strong antigenicity, no variable region might at any time be represented on a large enough number of bacterial cells, or otherwise be expressed long enough, to become immunodominant. Indeed, within the first 4 days PI, as many as 11 predicted amino acid changes per VlsE variant can occur during a B. burgdorferi B31 infection in C3H/HeN mice [Zheng, cited above], and unlike with T. brucei, N. gonorrhoeae and B. hermsii, VlsE serotypes of B. burgdorferi have never been found.

Our finding that IR$_6$ is exposed on the VlsE surface (FIG. 5) but not on the spirochetal surface (FIG. 6) is in agreement with the antigenicity and immunodominance of this region. Features of protein domains such as surface accessibility, hydrophilicity, flexibility and proximity to a site recognized by helper T cells are all important in positively determining domain antigenicity [J. A. Berzofsky and I. J. Berkower, Immunogenicity and antigen structure, in "Fundamental Immunology", William E. Paul, Editor, Raven Press, Ltd., New York, 235–282 (1993)]. Save for the possibility that solubilization with Triton X-100 may have partially denatured VlsE and thus artificially exposed IR$_6$, the result of the immune precipitation experiment indicates that IR$_6$ is accessible on the surface of native VlsE. It is also hydrophilic, as assessed by the Hopps-Wood algorithm. The molecular surface exposure of IR$_6$ was also indicated by the fact that a small proportion of unfixed spirochetes fluoresced when incubated with FITC-labeled anti-C$_6$ Ab (FIG. 6A).

Most of the unfixed spirochetes failed to label with the FITC-conjugated anti-C$_6$ Ab (FIG. 6). This indicates that IR$_6$ is not exposed on the spirochetal surface. The small proportion of unfixed spirochetes that bound anti-C$_6$ Ab likely had some degree of membrane damage. Although our procedure for labeling of unfixed spirochetes entailed very gentle manipulations, it is possible that portions of the VlsE molecule not normally exposed on the spirochete surface were nonetheless uncovered in a fraction of the spirochetes. The fragility of the outer membrane of B. burgdorferi has been noted by other investigators [D. L. Cox et al, Proc. Natl. Acad. Sci. USA, 93:7973–7978 (1996)]. Loss of the lp28-1 plasmid, which encodes VlsE, during in vitro cultivation [Zhang, Cell, 89:275–285 (1997)], also could explain a negative labeling result. However, the fact that nearly 100% of acetone-fixed spirochetes from the same culture were labeled allows us to rule out this possibility. Acetone fixation probably exposed regions of the VlsE not accessible to Ab on an intact spirochete.

The result of the ADCK experiment was entirely consistent with our interpretation of the immunofluoroescent observations, as absence of killing is most likely due to failure of the anti-$C_6$ Ab to bind to the spirochetal surface. Complement dependent killing of *B. burgdorferi* is facilitated by anti-surface Ab binding and does not depend on the C-activating properties of the Ab. *B. burgdorferi* spirochetes are able to activate complement through an Ab-independent mechanism [S. M. Kochi et al, Infect. Immun., 61:2532–2536 (1993)]. Taken together, our immunofluorescence and ACDK results indicate that $IR_6$ is cryptic on the spirochetal surface.

While the variable regions of Ags such as the VSG, Vmp or pilin are extremely antigenic, no strong antigenicity of these molecules' invariable regions or their longer invariable domains has been reported [D. M. Reinitz et al, Mol. Biochem. Parasitol., 51:119–132 (1992); K. T. Forest et al, Infect. Immun., 64:644–652 (1996)]. The principal role ascribed to both invariable regions and domains has been the preservation of functional molecular conformations [Reinitz, cited above; Forest, cited above]. What then is the role of the antigenicity and immunodominance of $IR_6$? It has been hypothesized that chronic host exposure to immunodominant Ags or epitopes diverts the immune system from responding to less antigenic but functionally important Ags or epitopes, thus serving as a protective strategy for persistent pathogens [P. Marrack and J. Kappler, Cell, 76:323–332 (1994)]. Recently, it was demonstrated that when the immunodominant V3 loop epitope of glycoprotein 120 (gp 120) of human immunodeficiency virus-1 is masked through site-directed targeting of N-linked glycosylation, the dominant, type-specific neutralizing Ab response is shifted away from V3 to epitopes in the first variable domain (V1) of gp120 [R. R. Garrity et al, J. Immunol., 159:279–289 (1997)]. Ab responses to conserved domains of gp120 also were observed [Garrity et al, cited above].

We submit that $IR_6$ may act as a decoy epitope and contribute to subvert the Ab response to *B. burgdorferi*. As mentioned before, it is conceivable that the promiscuity of VlsE antigenic variation in such that variable regions of VlsE do not, or not always, become immunodominant. The variation may serve to inhibit the formation of high avidity Abs to the variable VlsE regions, but not to divert the response away from invariable VlsE regions and invariable domains or other less antigenic but functionally neutralizing *B. burgdorferi* Ag. It should be considered that only about half of the length of the mature VlsE protein is variable, compared to more than two thirds of proteins such as VSG, pilin or VMP. Moreover, more than half of the variable domain of VlsE is encompassed by invariable regions including one highly immunodominant $IR_6$ just identified in this study. Conserved regions of VlsE other than $IR_6$ thus may be exposed, per force, on the spirochete surface. $IR_6$ would serve as the decoy epitope for such domains, by suppressing protective immune responses through mechanisms such as clonal restriction and/or idiotypic dysregulation, as has been invoked for HIV-1's V3 [H. Kohler et al, J. Acquired Immune Defic. Syndr., 5:1158–1168 (1993); R. Metals and V. Veljkovic, Vaccine, 13:355–359 (1995)].

EXAMPLE 8

An $IR_6$-Based ELISA for Diagnosis of Lyme Disease

To examine diagnostic specificity of the peptide ELISA, a serum panel of 99 specimens was obtained blindly from patients of a hospital in Louisiana, where Lyme disease is not endemic. A panel of 55 serum specimens from patients with multiple sclerosis, positive anticardiolipin antibody, positive rheumatoid factor, positive rapid plasma reagin, positive antinuclear antibody, Guillain-Barré syndrome or mycobacterial infection were obtained from the NIH. In addition, serum samples from 9 patients with relapsing fever were kindly provided by Dr. Barbara J. B. Johnson of the CDC, and 12 syphilis serum samples, (9 from patients with early latent and 3 with late latent disease) were kindly provided by Dr. James Miller of the University of California at Los Angeles.

Sensitivity was defined as True Positive/True Positive+ False Negatives, Specificity as True Negatives/True Negatives+False Positives, Positive Predictive Value as True Positives/True Positives+False Positives, and Negative Predictive Value as True Negatives/True Negatives+False Negatives.

A. Materials and Methods

Rhesus monkeys (2 to 4-year-old, *Macaca mulatta*) were infected by the bite of *Ixodes scapularis* nymphal ticks, as previously described [Philipp et al., Infect. Immun., 61:3047–3059 (1993)]. Animals were inoculated with spirochetes of either the JD1 (Philipp et al, 1993, cited above) or B31 [Philipp et al, Vaccine, 15:1872–1887 (1997)] strains of *B. burgdorferi* sensu stricto. Blood specimens were collected every one or two weeks postinoculation and serum samples were stored at −20° C. until the peptide ELISA was conducted.

Human serum samples were obtained from a variety of sources. To assess diagnostic sensitivity, three serum panels from Lyme disease patients were used. One was from the Centers for Disease Control and Prevention, kindly provided by Dr. Martin Schriefer; a second panel was from patients of the National Institutes of Health hospital and a third one from Tufts-New England Medical Center. The CDC serum panel was composed of 31 samples from patients with early Lyme disease and 10 from chronic patients. All of the serum specimens in this panel were from patients whose case satisfied the CDC Lyme disease case definition (Morb. Mort.). The NIH panel was composed of 18 specimens obtained from patients with chronic Lyme disease. The panel from Tufts-New England Medical Center was composed of 150 specimens, of which 39 were from patients in the accute phase of Lyme disease, 39 from individuals in the covalescent phase, 20 from patients who had presented with signals and/or symptoms of early neuroborreliosis, and 60 from patients with chronic Lyme disease (50 with Lyme arthritis, and 10 with late neuroborreliosis)

The $C_6$ peptide was synthesized as described in Example 1 above. The peptide ELISA was performed as described in Example 1 above. The cut-off OD (0.500) value was defined as the mean OD+3 standard deviations of 97 serum samples collected from patients of a Louisiana hospital (where Lyme disease is not endemic).

B. Early and Persisting IgG Response to $C_6$ in Infected Rhesus Monkeys

Figure 7A:
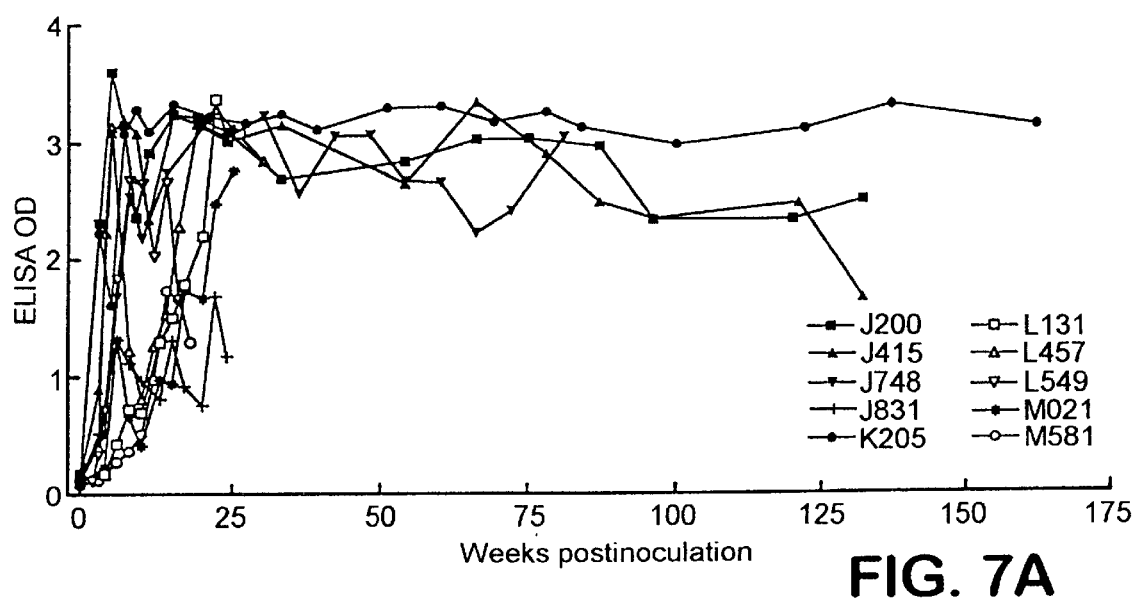
FIGS. 7A–7C illustrate the monkey response directed against $C_6$, an artificial peptide of the invention having the sequence of $IR_6$ and an N-terminal cysteine. The last point of each curve was the time when the monkey was sacrificed. All era were diluted 1:200. J831 and L131 were infected with JD1; L457 and M021 with B31. See, Example 8.
Figure 7B:
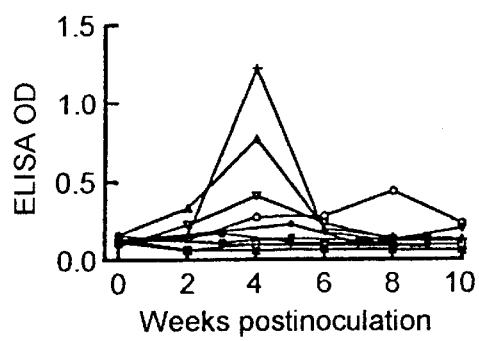
Figure 7C:
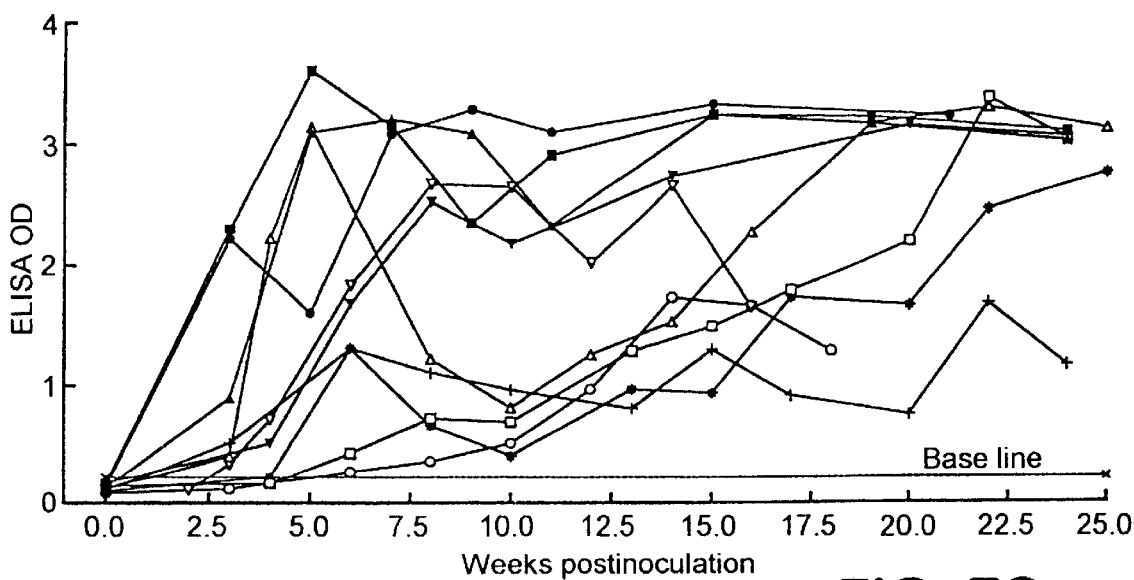

Serum samples serially collected from ten monkeys that had been inoculated either with the B31 or the JD1 strains of *B. burgdorferi* were tested by ELISA for antibody responses to $C_6$. IgG antibody was detectable in 6 animals as early as 2 weeks postinoculation and in the other animals between weeks 3 and 5 postinoculation (FIG. 7A). Antibody to $C_6$ remained at high levels in all animals during the entire study period, which was between 25 and 160 weeks (FIG. 7B). Only the serum samples from JD1-infected monkeys are shown. The IgM responses were detectable only in some of the animals and did not appear earlier than the corresponding IgG responses (FIG. 7C).

C. Sensitivity of the $C_6$ ELISA

Thirty-one serum samples obtained by the CDC from patients with acute Lyme borreliosis were assessed with the $C_6$ ELISA.

TABLE 3

Sensitivity of $C_6$ ELISA

| Panel # | Infection Course | Sample No. | Positive | Negative | Sensitivity (%) |
|---|---|---|---|---|---|
| 1 | CDC acute | 31 | 25 | 6 | 81 |
|   | CDC chronic | 10 | 10 | 0 | 100 |
| 2 | Acute | 39 | 29 | 10 | 74 |
|   | Convalescent | 39 | 35 | 4 | 90 |
|   | Early neuroborreliosis | 20 | 19 | 1 | 95 |
|   | Lyme arthritis | 50 | 49 | 1 | 98 |
|   | Late neuroborreliosis | 10 | 10 | 0 | 100 |
| 3 | Chronic | 19 | 13 | 6 | 68 |
|   | Overall | 218 | 190 | 28 | 90 |

Twenty-five were positive (Table 3; FIG. 8A), thus yielding a sensitivity of detection of 81%. An assessment of the same samples performed at the CDC with commercially available assay kits yielded a sensitivity of 71% (22/31) with a conventional ELISA (Lyme Screen II, bioMerieux, St. Louis, Mo.), 48% (15/31) with an IgG immunoblot (Marblot, MarDx, Carlsbad, Calif.), 35% (11/31) with an IgM immunoblot (Marblot), and 71% (22/31) with the combination of both IgG and IgM immunoblots. Testing of 10 CDC serum samples from chronic Lyme borreliosis patients yielded a sensitivity of 100% (10/10) with the $C_6$ ELISA (Table 3, FIG. 8A). These samples were also 100% positive either by conventional ELISA or IgG Western Blot (WB).

One hundred and fifty-nine additional serum samples collected from patients with different phases of Lyme disease at Tufts-New England Medical Center also were assessed with the $C_6$ ELISA. The sensitivity was 74% (29/39) for patients in the acute disease phase, 90% (35/39) for convalescent-phase patients, 95% (19/20) for early neuroborreliosis, 98% (49/50) for Lyme arthritis, and 100% (10/10) for late neuroborreliosis patients, respectively (Table 3, FIG. 8A). An additional test of 18 serum specimens collected from patients with chronic Lyme disease yielded a sensitivity of 68% (13/19) (Table 3, FIG. 8)

The IgM response to $C_6$ also was examined with serum specimens collected during early infections. All IgM positive sera had a detectable IgG response (data not shown).

The sensitivity of the $C_6$ ELISA ranged from 68% to 100% depending on when in the course of infection the serum samples were collected, and on the source of the samples (Table 3). Based on the results of our longitudinal analysis of the anti-$C_6$ antibody response in infected rhesus monkeys (FIG. 7), it is unlikely that such a response may be detectable earlier than two to three weeks postinfection. This may explain why lower sensitivity results were associated mostly with early Lyme disease serum specimens, many of which were culture-confirmed. With the CDC serum panel of 31 early specimens, the sensitivity of $C_6$ ELISA (81%) was higher than that of the conventional ELISA (71%). The lowest sensitivity that was obtained with serum specimens collected during the acute phase of Lyme disease was 74%, with the 39 samples from Tufts-New England Medical Center. In contrast, with the 20 early-neuroborreliosis specimens the sensitivity was as high as 95%. We also explored the possibility of making an earlier diagnosis by testing IgM responses to $C_6$ using antihuman-IgM-peroxidase conjugate as a second-antibody probe. All positive IgM samples also had a detectable IgG response (data not shown). This finding was in agreement with the results obtained with infected monkey serum (FIG. 7), which showed that the IgM antibody response, when detectable, did not appear before the corresponding IgG antibody response.

Overall, and as expected from the results obtained with rhesus monkeys as diseased progressed in these animals, sensitivity of anti-$C_6$ antibody detection was higher ($\geq 98\%$) in chronic patients (Table 3). The exceptions were the samples from the NIH, which were only 68% positive with the $C_6$ ELISA. The overall sensitivity when all of the samples were considered was 90%.

C. Specificity of $C_6$ ELISA

The $C_6$ ELISA yielded a specificity of 100% when serum samples from patients with other chronic infections or autoimmune diseases were tested (Table 4; FIG. 8B).

TABLE 4

Specificity of $C_6$ ELISA

| Sample Description | Sample No. | Positive | Negative | Specificity (%) |
|---|---|---|---|---|
| Relapsing fever | 9 | 0 | 9 | 100 |
| Syphilis | 12 | 0 | 12 | 100 |
| MS | 10 | 0 | 10 | 100 |
| ACA | 10 | 0 | 10 | 100 |
| RF | 10 | 0 | 10 | 100 |
| RPR | 10 | 0 | 10 | 100 |
| ANA | 10 | 0 | 10 | 100 |
| GBS | 1 | 0 | 1 | 100 |
| Myco | 5 | 0 | 5 | 100 |
| Hospitalized patient | 99 | 2 | 97 | 98 |
| Overall | 176 | 2 | 174 | 99 |

MS, multiple sclerosis; ACA, positive anticardiolipin antibody; RF, positive rheumatoid factor; RFR, positive rapid plasma reagin; ANA, positive antinuclear antibody; GBS, Guillain-Barré syndrome; Myco, mycobacterial infection.

This panel included 9 specimens from relapsing fever patients (CDC), 12 syphilis patient samples (UCLA), and 55 specimens from patients with multiple sclerosis, positive anticardiolipin antibody, positive rheumatoid factor, positive rapid plasma reagin, positive antinuclear antibody, Guillain-Barré syndrome or mycobacterial infection (NIH). Only two potential false positive results were obtained when a group of 99 human serum samples randomly collected at a local hospital in Louisiana, USA, were tested (Table 4; FIG. 8B). Lyme disease is not endemic in Louisiana, but the identity of the patients and their clinical history is unknown.

This data demonstrates that the $C_6$ ELISA is remarkably specific (Table 4). It could discriminate between Lyme borreliosis and infections with spirochetes of different species but the same genus (*B. hermsii*) or family (*T. pallidum*). Moreover, none of the samples from patients with autoimmune diseases or diseases that often need to be differently diagnosed with respect to Lyme disease, such as multiple sclerosis or the Guillain-Barré syndrome were positive with the $C_6$ test. Only 2 of 99 serum samples from a local hospital in Louisiana, where Lyme disease is not edemic, yielded a positive $C_6$ ELISA result. Since the samples were collected randomly from unknown patients, it is impossible to assess whether these two patients could have been exposed to *B. burgdorferi*. The specificity results obtained are supported by our finding that, except for the Vls cassette of Lyme spirochetes, no other sequences homologous to $C_6$ could be identified (using the BLAST search algorithm) in the National Center for Biotechnology Information protein sequence data base. High diagnostic specificity is extremely critical to improve the positive predictive value of a test, especially when the prevalence of a disease is very low. The prevalence of Lyme disease in most endemic areas is less than 0.01% [Lightfoot et al., Ann Intern Med., 119:503–509 (1993); Tugwell et al, Ann Intern Med., 127:1109–1123 (1997)]. The overall specificity of the $C_6$ ELISA was 99% and the positive and negative predictive values were 99% and 89%, respectively.

The cassette portion of the VlsE contains 6 invariable regions (IR) interspersed with an equal number of variable regions [Zhang et al., Cell, 89:275–285 (1997)]. The latter, by their very nature, have no diagnostic value. The additional 5 IRs are not as conserved as $IR_6$. Nonetheless, we assessed whether the remaining IRs ($IR_{1-5}$) could contribute to improve the diagnostic performance of $C_6$, whose sequence is based on that of $IR_6$. No antibody responses to peptides reproducing the sequences of $IR_{1-5}$ were detected in humans or monkeys infected with *B. burgdorferi* (data not shown). On this basis we concluded that no improvements would be accrued from incorporating any of these peptides into the assay.

As expected, monkey serum samples which contained high-titer anti-OspA antibody did not react with $C_6$. This ELISA, therefore, is suitable in the OspA-vaccine sera. Moreover, because of its simplicity and high specificity and sensitivity, it alleviates the so-far intractable problems of Lyme disease serodiagnosis.

All above-noted references and priority document are incorporated herein by reference. Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. An isolated, recombinant or synthetic peptide consisting of the immunodominant invariable region 6 of the VlsE protein isolated from a borrelia species that causes Lyme borreliosis, wherein said peptide binds in a mammalian biological sample antibodies specific to the causative agent of Lyme borreliosis.

2. An isolated, recombinant or synthetic peptide consisting of the immunodominant invariable region 6 of the VlsE protein isolated from a borrelia species that causes Lyme borreliosis, said peptide consisting of SEQ ID NO: 1.

3. A modified peptide of the immunodominant invariable region 6 of the VlsE protein of SEQ ID NO: 1, wherein one or more amino acids selected from the group consisting of D4, M11, V12, Q21, and L24 of SEQ ID NO: 1 are substituted with a conservative amino acid replacement.

4. An isolated, recombinant or synthetic peptide consisting of the immunodominant invariable region 6 of the VlsE protein isolated from a borrelia species that causes Lyme borreliosis, said peptide consisting of amino acid residues 241–266 of SEQ ID NO: 11.

5. An isolated, recombinant or synthetic peptide consisting of the immunodominant invariable region 6 of the VlsE protein isolated from a borrelia species that causes Lyme borreliosis, said peptide consisting of amino acid residues 150–175 of SEQ ID NO: 10.

6. An isolated, recombinant or synthetic peptide consisting of the immunodominant invariable region 6 of the VlsE protein isolated from a borrelia species that causes Lyme borreliosis, wherein said peptide binds in a mammalian biological sample antibodies specific to the causative agent of Lyme borreliosis, wherein said sequence is coupled or fused to a second moiety via an optional terminal amino acid linker or chemical coupling agent.

7. The peptide of claim 6, wherein said terminal amino acid linkers is selected from the group consisting of Lys and Cys.

8. The peptide of claim 6, wherein said second moiety is a detectable label.

9. The peptide of claim 6, wherein said second moiety is an immunogenic carrier.

10. The peptide of claim 6, wherein said second moiety is a fusion partner.

11. The peptide of claim 6, wherein said second moiety is a substrate that immobilizes said peptide.

12. The peptide of claim 10, wherein the fusion partner is selected from the group consisting of SEQ ID NO: 3, SEQ ID NO: 4, SEQ ID NO: 5, SEQ ID NO: 6 and SEQ ID NO: 7.

13. A peptide selected from the group consisting of:
(a). a peptide consisting of SEQ ID NO: 1
(b). the peptide of (a), wherein an amino acid is added to the amino or carboxyl terminus thereof, and
(c). the peptide of (a), wherein an amino acid is deleted from the amino or carboxyl terminus thereof,
wherein each peptide (a) through (c) binds in a mammalian biological sample antibodies specific to the causative agent of Lyme disease.

14. The peptide of claim 13, which consists of amino acid residues 1 to 25 of SEQ ID NO: 1.

15. The peptide of claim 13 consisting of SEQ ID NO: 8.

16. A peptide selected from the group consisting of:
(a). a peptide consisting of amino acid residues 241–266 of SEQ ID NO: 11, wherein an amino acid is deleted from the amino or carboxyl terminus thereof, and
(b). a peptide consisting of amino acid residues 241–266 of SEQ ID NO: 11, wherein an amino acid is added to the amino or carboxyl terminus thereof,
wherein each peptide (a) through (b) binds in a mammalian biological sample antibodies specific to the causative agent of Lyme disease.

17. A peptide selected from the group consisting of:
(a). a peptide consisting of amino acid residues 150–175 of SEQ ID NO: 12, wherein an amino acid is deleted from the amino or carboxyl terminus thereof, and
(b). a peptide consisting of amino acid residues 150–175 of SEQ ID NO: 12, wherein an amino acid is added to the amino or carboxyl terminus thereof,
wherein each peptide (a) through (b) binds in a mammalian biological sample antibodies specific to the causative agent of Lyme disease.

18. A diagnostic reagent comprising a peptide consisting of the immunodominant invariable region 6 of the VlsE protein isolated from a borrelia species that causes Lyme borelliosis, which peptide binds to antibodies specific to the causative agent of Lyme borreliosis, in a mammalian biological sample, and a second moiety selected from the group consisting of a detectable level and a substrate for immobilizing said peptide.

19. The diagnostic reagent of claim 18 comprising a peptide and a second moiety selected from the group consisting of a detectable label and a substrate for immobilizing, wherein the peptide is selected from the group consisting of
(a). a peptide consisting of SEQ ID NO: 1,
(b). a modified peptide of (a), wherein one or more amino acids selected from the group consisting of D4, M11, V12, Q21, and L24 of SEQ ID NO: 1 are substituted with a conservative amino acid replacement,
(c). a peptide consisting of amino acid residues 241–266 of SEQ ID NO: 11,
(d). a peptide consisting of amino acid residues 150–175 of SEQ ID NO: 10,
(e). a peptide of (a) through (d), wherein an amino acid is deleted from the amino or carboxyl terminus thereof,
(f). a peptide of (a) through (d) wherein an amino acid is added to the amino or carboxyl terminus thereof,
wherein each peptide (a) through (f) binds antibodies in a mammalian biological sample specific to the causative agent of Lyme disease.

20. The reagent of claim 18, wherein said label is biotin.

21. The reagent of claim 18, wherein said immobilizing substrate is selected from the group consisting of a microwell plate, a nitrocellulose membrane and latex beads.

22. A composition comprising a peptide, wherein said peptide binds in a mammalian biological sample to antibodies specific to the causative agent of Lyme borreliosis, said peptide selected from the group consisting of:
(a). a peptide consisting of SEQ ID NO: 1,
(b). the peptide of (a), wherein one or more amino acids selected from the group consisting of D4, M11, V12, Q21, and L24 of SEQ ID NO: 1 are replaced with a conservative residue amino acid substitution,
(c). a peptide consisting of amino acid residues 241–266 of SEQ ID NO: 11,
(d). a peptide consisting of amino acid residues 150–175 of SEQ ID NO: 10, and
(e). the peptides of (a) through (d), wherein an amino acid deleted is deleted from the carboxyl terminus thereof,
(f). the peptides of (a) through (d), wherein an amino acid is added to the carboxyl terminus thereof,
wherein each peptide (a) through (f) binds in a mammalian biological sample antibodies specific to the causative agent of Lyme disease.

23. A composition comprising a peptide consisting of the immunodominant invariable region 6 of the VlsE protein isolated from a borrelia species that causes Lyme borreliosis, wherein said peptide binds in a mammalian biological sample antibodies specific to the causative agent of Lyme borreliosis, a second borrelia antigen selected from the group consisting of OspA, OspB, OspC, BmpA, BmpB, BmpC, and BmpD of *B. burgdorferi,* and a pharmaceutically acceptable carrier.

24. A kit for diagnosing Lyme borreliosis in a human or animal comprising a peptide consisting of the immunodominant invariable region 6 of the VlsE protein isolated from a borrelia species that causes Lyme borreliosis, wherein said peptide binds in a mammalian biological sample antibodies specific to the causative agent of Lyme borreliosis, and at least one component selected from the group consisting of a detectable label which produces a detectable signal and a substrate which immobilizes said peptide.

25. A kit for diagnosing Lyme borreliosis in a human or animal comprising a peptide, wherein said peptide binds in a mammalian biological sample antibodies specific to the causative agent of Lyme borreliosis and is selected from the group consisting of:

(a). a peptide consisting of SEQ ID NO: 1, (b). a modified peptide of (a), wherein one or more amino acids selected from the group consisting of D4, M11, V12, Q21, and L24 of SEQ ID NO: 1 are substituted with a conservative amino acid replacement, (c). a peptide consisting of amino acid residues 241–266 of SEQ ID NO: 11, (d). a peptide consisting of amino acid residues 150–175 of SEQ ID NO: 10, (e). a peptide of (a) through (d) wherein an amino acid is deleted from the amino or carboxyl terminus thereof, (f). a peptide of (a) through (d) wherein an amino acid is added to the amino or carboxyl terminus thereof, wherein each peptide (a) through (f) binds in a mammalian biological sample antibodies specific to the causative agent of Lyme disease, and at least one other additional component selected from the group consisting of a detectable label and a substrate which immobilizes said peptide.

26. A kit for diagnosing Lyme borreliosis in a human or animal comprising the peptide consisting of SEQ ID NO: 1 and at least one component selected from the group consisting of a detectable label and a substrate which immobilizes said peptide.

27. The kit of claim 24, wherein said immobilizing substrate is selected from the group consisting of a microwell plate, a nitrocellulose membrane and latex beads.

28. The kit of claim 24, further comprising a labeled conjugate for detection, and a signal generating reagent.

* * * * *

UNITED STATES PATENT AND TRADEMARK OFFICE
CERTIFICATE OF CORRECTION

PATENT NO. : 6,475,492 B1
DATED : November 5, 2002
INVENTOR(S) : Phillipp et al.

It is certified that error appears in the above-identified patent and that said Letters Patent is hereby corrected as shown below:

Title page,
Item [57], ABSTRACT,
Line 2, replace "conversed" with -- conserved --.

Column 2,
Line 7, replace "MAKDGOALKD" with -- MAKDGOFALKD --.

Column 3,
Line 40, insert after "EGAIKG" -- (SEQ ID NO: 2) --.
Line 40, replace "single" with -- singly --.
Line 52, replace "181" with -- 184 --.

Column 5,
Line 35, replace "NO:8]" with -- NO:1] --.
Line 38, replace "so" with -- of --.

Column 8,
Line 50, replace "following" with -- followed --.

Column 9,
Line 6, replace "grade" with -- encode --.
Line 19, delete "was".
Line 56, replace "liked" with -- linked --.

Column 15,
Line 43, replace "i" with -- in --.

Column 16,
Line 22, replace "may be maybe" with -- may be made by --.
Line 57, replace "pluraonic" with -- pluronic --.

Column 17,
Line 6, replace "determine" with -- determined --.
Line 9, replace "L" with -- mL --.
Line 15, replace "does" with -- doses --.

UNITED STATES PATENT AND TRADEMARK OFFICE
CERTIFICATE OF CORRECTION

PATENT NO. : 6,475,492 B1
DATED : November 5, 2002
INVENTOR(S) : Phillipp et al.

It is certified that error appears in the above-identified patent and that said Letters Patent is hereby corrected as shown below:

Column 19,
Line 32, replace "lysate" with -- insert --.
Line 60, replace "4 N $H_2 SO_4$" with -- $4NH_2 SO_4$ --.

Column 23,
Line 36, replace "reside" with -- residue --.

Column 25,
Line 42, replace "accessible" with -- inaccessible --.

Column 27,
Line 13, replace "ACDK" with -- ADCK --.

Column 28,
Lines 45-46, replace "covalescent" with -- convalescent --.

Column 30,
Line 59, replace "differently" with -- differentially --.

Column 40,
Line 20, replace "level" with -- label --.

Signed and Sealed this

Twenty-eighth Day of October, 2003

JAMES E. ROGAN
*Director of the United States Patent and Trademark Office*

SEQUENCE LISTING

<160> NUMBER OF SEQ ID NOS: 11

<210> SEQ ID NO 1
<211> LENGTH: 26
<212> TYPE: PRT
<213> ORGANISM: Borrelia garinii

<400> SEQUENCE: 1

```
Met Lys Lys Asp Asp Gln Ile Ala Ala Ala Met Val Leu Arg Gly Met
1               5                   10                  15

Ala Lys Asp Gly Gln Phe Ala Leu Lys Asp
            20                  25
```

<210> SEQ ID NO 2
<211> LENGTH: 6
<212> TYPE: PRT
<213> ORGANISM: Borrelia burgdorferi

<400> SEQUENCE: 2

```
Glu Gly Ala Ile Lys Gly
1               5
```

<210> SEQ ID NO 3
<211> LENGTH: 9
<212> TYPE: PRT
<213> ORGANISM: Borrelia garinii

<400> SEQUENCE: 3

```
Gly Asn Ala Ala Ile Gly Asp Val Val
1               5
```

<210> SEQ ID NO 4
<211> LENGTH: 16
<212> TYPE: PRT
<213> ORGANISM: Borrelia garinii

<400> SEQUENCE: 4

```
Ser Val Asn Gly Ile Ala Lys Gly Ile Lys Gly Ile Val Asp Ala Ala
1               5                   10                  15
```

<210> SEQ ID NO 5
<211> LENGTH: 7

```
<212> TYPE: PRT
<213> ORGANISM: Borrelia garinii

<400> SEQUENCE: 5

Ala Gly Lys Leu Phe Val Lys
1               5

<210> SEQ ID NO 6
<211> LENGTH: 25
<212> TYPE: PRT
<213> ORGANISM: Borrelia garinii

<400> SEQUENCE: 6

Asp Ala Gly Lys Ala Ala Ala Val Ala Ala Val Ser Gly Glu Gln
1               5                   10                  15

Ile Leu Lys Ala Ile Val His Ala Ala
            20                  25

<210> SEQ ID NO 7
<211> LENGTH: 10
<212> TYPE: PRT
<213> ORGANISM: Borrelia garinii

<400> SEQUENCE: 7

Ala Thr Asn Pro Ile Asp Ala Ala Ile Gly
1               5                   10

<210> SEQ ID NO 8
<211> LENGTH: 26
<212> TYPE: PRT
<213> ORGANISM: Borrelia garinii

<400> SEQUENCE: 8

Cys Met Lys Lys Asp Asp Gln Ile Ala Ala Ala Met Val Leu Arg Gly
1               5                   10                  15

Met Ala Lys Asp Gly Gln Phe Ala Leu Lys
            20                  25

<210> SEQ ID NO 9
<211> LENGTH: 349
<212> TYPE: PRT
<213> ORGANISM: Borrelia garinii

<400> SEQUENCE: 9

Lys Asn Asn Asp His Asp Asn His Lys Gly Thr Val Lys Asn Ala Val
1               5                   10                  15

Asp Met Ala Lys Ala Ala Glu Glu Ala Ala Ser Ala Ala Ser Ala Ala
            20                  25                  30

Thr Gly Asn Ala Ala Ile Gly Asp Val Val Lys Asn Ser Gly Ala Ala
        35                  40                  45

Ala Lys Gly Gly Glu Ala Ala Ser Val Asn Gly Ile Ala Lys Gly Ile
    50                  55                  60

Lys Gly Ile Val Asp Ala Ala Lys Ala Asp Ala Lys Glu Gly Lys
65                  70                  75                  80

Leu Asp Ala Thr Gly Ala Glu Gly Thr Thr Asn Val Asn Ala Gly Lys
                85                  90                  95

Leu Phe Val Lys Arg Ala Ala Asp Asp Gly Asp Ala Asp Ala
            100                 105                 110

Gly Lys Ala Ala Ala Ala Val Ala Ala Ser Ala Ala Thr Gly Asn Ala
        115                 120                 125
```

```
Ala Ile Gly Asp Val Val Asn Gly Asp Val Ala Lys Ala Lys Gly Gly
        130                 135                 140

Asp Ala Ala Ser Val Asn Gly Ile Ala Lys Gly Ile Lys Gly Ile Val
145                 150                 155                 160

Asp Ala Ala Glu Lys Ala Asp Ala Lys Glu Gly Lys Leu Asn Ala Ala
                165                 170                 175

Gly Ala Glu Gly Thr Thr Asn Ala Asp Ala Gly Lys Leu Phe Val Lys
            180                 185                 190

Asn Ala Gly Asn Val Gly Gly Glu Ala Gly Asp Ala Gly Lys Ala Ala
        195                 200                 205

Ala Ala Val Ala Ala Val Ser Gly Glu Gln Ile Leu Lys Ala Ile Val
    210                 215                 220

His Ala Ala Lys Asp Gly Gly Lys Gln Gly Lys Lys Ala Ala Asp
225                 230                 235                 240

Ala Thr Asn Pro Ile Asp Ala Ala Ile Gly Gly Ala Gly Asp Asn Asp
                245                 250                 255

Ala Ala Ala Ala Phe Ala Thr Met Lys Lys Asp Asp Gln Ile Ala Ala
            260                 265                 270

Ala Met Val Leu Arg Gly Met Ala Lys Asp Gly Gln Phe Ala Leu Lys
        275                 280                 285

Asp Ala Ala Ala His Glu Gly Thr Val Lys Asn Ala Val Asp Ile
    290                 295                 300

Ile Lys Ala Ala Ala Glu Ala Ala Ser Ala Ala Ser Ala Ala Thr Gly
305                 310                 315                 320

Ser Ala Ala Ile Gly Asp Val Val Asn Gly Asn Gly Ala Thr Ala Lys
                325                 330                 335

Gly Gly Asp Ala Lys Ser Val Asn Gly Ile Ala Lys Gly
                340                 345

<210> SEQ ID NO 10
<211> LENGTH: 189
<212> TYPE: PRT
<213> ORGANISM: Borrelia burgdorferi

<400> SEQUENCE: 10

Ala Thr Glu Ala Ala Thr Ala Ala Ser Gly Asp Lys Glu Met Ile Gly
1               5                   10                  15

Lys Val Val Lys Val Thr Asn Ala Gly Ala Ala Ala Lys Gly Gly
            20                  25                  30

Glu Glu Lys Ser Val Asn Gly Ile Ala Ser Gly Ile Lys Gly Ile Val
        35                  40                  45

Glu Ala Ala Glu Lys Ala Gly Lys Glu Gly Lys Leu Glu Ala Ala Ala
    50                  55                  60

Gly Asp Gly Asn Lys Asp Ala Cys Ala Gly Lys Leu Phe Ala Lys Asn
65                  70                  75                  80

Ala Ala Asn Gly Gly Gly Ala Ala Ala Glu Lys Ala Ala Ala
            85                  90                  95

Ala Val Ser Ala Val Ser Gly Lys Gln Ile Leu Lys Ala Ile Val Asp
                100                 105                 110

Ala Ala Gly Lys Glu Glu Lys Gly Val Ala Asp Val Lys Glu Ala Thr
            115                 120                 125

Asn Pro Ile Glu Ala Ala Ile Gly Ser Thr Gly Asp Asn Asp Ala Ala
        130                 135                 140

Ala Phe Gln Asp Glu Met Lys Lys Asn Asp Gln Ile Ala Ala Ala Ile
145                 150                 155                 160
```

-continued

Val Leu Arg Gly Met Ala Lys Asp Gly Glu Phe Ala Leu Lys Asp Asn
                165                 170                 175

Glu His Asp Lys Ala Lys Gly Leu Lys Ser Thr Val Glu
            180                 185

<210> SEQ ID NO 11
<211> LENGTH: 323
<212> TYPE: PRT
<213> ORGANISM: Borrelia burgdorferi

<400> SEQUENCE: 11

Ala Val Ser Gly Glu Gln Ile Leu Ser Ala Ile Val Lys Ala Ala Ala
1               5                   10                  15

Ala Gly Ala Ala Asp Gln Asp Gly Glu Lys Pro Gly Asp Ala Lys Asn
            20                  25                  30

Pro Ile Ala Ala Ile Gly Lys Gly Asn Ala Asp Asp Gly Ala Asp
        35                  40                  45

Phe Gly Asp Gly Met Lys Lys Asp Asp Gln Ile Ala Ala Ile Ala
    50                  55                  60

Leu Arg Gly Met Ala Lys Asp Gly Lys Phe Ala Val Lys Lys Asp Glu
65                  70                  75                  80

Lys Gly Lys Ala Glu Gly Ala Ile Lys Gly Ala Ser Glu Leu Leu Asp
                85                  90                  95

Lys Leu Val Lys Ala Val Lys Thr Ala Glu Gly Ala Ser Ser Gly Thr
            100                 105                 110

Ala Ala Ile Gly Glu Val Val Asp Asn Ala Ala Lys Ala Ala Asp Lys
            115                 120                 125

Asp Ser Val Thr Gly Ile Ala Lys Gly Ile Lys Glu Ile Val Glu Ala
        130                 135                 140

Ala Gly Gly Ser Glu Lys Leu Lys Val Ala Ala Lys Gly Glu Asn
145                 150                 155                 160

Asn Lys Gly Ala Gly Lys Leu Phe Gly Lys Ala Gly Ala Asn Ala His
                165                 170                 175

Gly Asp Ser Glu Ala Ala Ser Lys Ala Ala Gly Ala Val Ser Ala Val
            180                 185                 190

Ser Gly Glu Gln Ile Leu Ser Ala Ile Val Lys Ala Ala Gly Glu Ala
        195                 200                 205

Gly Asp Gln Glu Gly Lys Lys Pro Glu Glu Ala Lys Asn Pro Ile Ala
    210                 215                 220

Ala Ala Ile Gly Asp Lys Asp Gly Asp Ala Glu Phe Asn Gln Asp Gly
225                 230                 235                 240

Met Lys Lys Asp Asp Gln Ile Ala Ala Ile Ala Leu Arg Gly Met
                245                 250                 255

Ala Lys Asp Gly Lys Phe Ala Val Lys Asp Gly Gly Glu Lys Ala Glu
            260                 265                 270

Gly Ala Ile Lys Gly Val Ser Glu Leu Leu Asp Leu Val Lys Ala Val
        275                 280                 285

Lys Thr Ala Glu Gly Ala Ser Ser Gly Thr Ala Ala Ile Gly Glu Val
    290                 295                 300

Val Ala Asp Ala Ala Lys Val Ala Asp Lys Ala Ser Val Thr Gly Ile
305                 310                 315                 320

Ala Lys Gly